(12) United States Patent
Saavedra et al.

(10) Patent No.: US 11,771,571 B2
(45) Date of Patent: Oct. 3, 2023

(54) MODULAR PROSTHETIC HAND SYSTEM

(71) Applicant: Alt-Bionics, Inc., San Antonio, TX (US)

(72) Inventors: Ryan Leo Saavedra, San Antonio, TX (US); Jackson Cole Heinz, Bellbrook, OH (US); Samuel Everett Woolfolk, Delta Junction, AK (US)

(73) Assignee: ALT-BIONICS, INC., San Antonio, TX (US)

( * ) Notice: Subject to any disclaimer, the term of this patent is extended or adjusted under 35 U.S.C. 154(b) by 0 days.

(21) Appl. No.: 17/852,119

(22) Filed: Jun. 28, 2022

(65) Prior Publication Data

US 2022/0409402 A1  Dec. 29, 2022

Related U.S. Application Data

(60) Provisional application No. 63/215,869, filed on Jun. 28, 2021.

(51) Int. Cl.
*A61F 2/70* (2006.01)
*A61F 2/54* (2006.01)
*A61F 2/72* (2006.01)
*B25J 15/08* (2006.01)
*A61F 2/58* (2006.01)
(Continued)

(52) U.S. Cl.
CPC .............. *A61F 2/583* (2013.01); *A61F 2/585* (2013.01); *A61F 2/586* (2013.01); *A61F 2/72* (2013.01); *B25J 15/0009* (2013.01); *B25J 15/0475* (2013.01); *A61F 2002/5083* (2013.01); *A61F 2002/587* (2013.01); *A61F 2002/701* (2013.01); *A61F 2002/763* (2013.01); *A61F 2002/769* (2013.01); *A61F 2002/7635* (2013.01)

(58) Field of Classification Search
CPC ............ B25J 15/0475; A61F 2002/769; A61F 2/586–2002/587
See application file for complete search history.

(56) References Cited

U.S. PATENT DOCUMENTS

| 4,114,464 A | 9/1978 | Schubert et al. |
| 8,936,290 B1 | 1/2015 | Salisbury et al. |
(Continued)

FOREIGN PATENT DOCUMENTS

| CN | 107280825 A | * 10/2017 | ............... A61F 2/54 |
| CN | 109620487 A | * 4/2019 | ............ A61F 2/585 |
(Continued)

OTHER PUBLICATIONS

"Bionic Hand Price List", [Online]. Retrieved from the Internet: URL: https: bionicsforeveryone.com bionic-hand-price-list , (Apr. 12, 2022), 5 pgs.
(Continued)

*Primary Examiner* — David H Willse
(74) *Attorney, Agent, or Firm* — SCHWEGMAN LUNDBERG & WOESSNER, P.A.

(57) ABSTRACT

Prosthetic devices, such as prosthetic hands (including, e.g., bionic prosthetic hands controlled by myoelectric signals and/or equipped with force sensors for feedback) can utilize a modular design to simplify assembly and repair. In some embodiments, low-cost additive manufacturing techniques are employed, e.g., to create prosthetic device parts with complex interior geometries and/or functionally integrated components.

19 Claims, 23 Drawing Sheets

(51) Int. Cl.
B25J 15/00 (2006.01)
B25J 15/04 (2006.01)
*A61F 2/50* (2006.01)
*A61F 2/76* (2006.01)

(56) References Cited

U.S. PATENT DOCUMENTS

| | | | |
|---|---|---|---|
| 8,999,003 | B2 | 4/2015 | Wenstrand et al. |
| 9,072,614 | B2* | 7/2015 | Starkey .................. A61F 2/586 |
| 10,219,919 | B2 | 3/2019 | Belter et al. |
| 10,271,966 | B2 | 4/2019 | Glasgow |
| 2006/0224249 | A1* | 10/2006 | Winfrey ................... A61F 2/70 623/64 |
| 2007/0213831 | A1 | 9/2007 | De Cubber |
| 2011/0257764 | A1 | 10/2011 | Herr et al. |
| 2014/0067083 | A1 | 3/2014 | Wenstrand et al. |
| 2014/0277588 | A1* | 9/2014 | Patt ........................ A61F 2/586 623/57 |
| 2018/0036145 | A1* | 2/2018 | Jury ........................ A61F 2/583 |
| 2019/0240047 | A1* | 8/2019 | Trojan .................... A61F 2/583 |
| 2019/0301570 | A1* | 10/2019 | Weir ........................ B33Y 80/00 |
| 2019/0380846 | A1 | 12/2019 | Lipsey et al. |
| 2020/0330246 | A1 | 10/2020 | Tognetti et al. |
| 2020/0405417 | A1 | 12/2020 | Shelton, IV et al. |
| 2021/0145610 | A1* | 5/2021 | Rivera .................... A61F 2/586 |

FOREIGN PATENT DOCUMENTS

| | | | | |
|---|---|---|---|---|
| CN | 111134917 A | * | 5/2020 | ............... A61F 2/54 |
| DE | 102014007743 | | 12/2015 | |
| JP | 2003-266357 A | * | 9/2003 | .......... B25J 15/0475 |
| RU | 2 727 893 C1 | * | 7/2020 | ............. A61F 2/586 |
| WO | 03017879 | | 3/2003 | |
| WO | WO-2010018358 A2 | | 2/2010 | |
| WO | WO-2016174243 A1 | | 11/2016 | |
| WO | 2018006722 | | 1/2018 | |
| WO | 2019166990 | | 9/2019 | |
| WO | 2019243945 | | 12/2019 | |
| WO | WO 2020/019992 A1 | * | 1/2020 | ............. A61F 2/586 |

OTHER PUBLICATIONS

Liow, Lois, "Olympic: A Modular, Tendon-Driven Prosthetic Hand with Novel Finger and Wrist Coupling Mechanisms", IEEE Robotics and Automation Letters vol. 5, Issue: 2, (Apr. 2020), 8 pgs.

Xu, Zhe, "A Low-cost and Modular, 20-DOF Anthropomorphic Robotic Hand: Design, Actuation and Moeling", 2013 13th IEEE-RAS International Conference on Humanoid Robots (Humanoids), (Oct. 2013), 8 pgs.

"International Application Serial No. PCT/US2022/035331, International Search Report dated Oct. 5, 2022", 3 pgs.

"International Application Serial No. PCT/US2022/035331, Written Opinion dated Oct. 5, 2022", 8 pgs.

"WO2010120404A2 Application as filed on Feb. 16, 2010", The published version on WIPO and Espace has misprinted pages., (Feb. 16, 2010), 177 pgs.

* cited by examiner

MODULAR PROSTHETIC HAND SYSTEM

CROSS-REFERENCE TO RELATED APPLICATION

This application claims the benefit of priority to U.S. Provisional Application No. 63/215,869, filed on Jun. 28, 2021, which is incorporated herein by reference in its entirety.

TECHNICAL FIELD

The present disclosure relates to prosthetic systems and devices, and more particularly, in some embodiments, to a modular bionic prosthetic hand device.

BACKGROUND

Many amputees who have lost limbs, e.g., due to disease, accident or other trauma, or congenital defect, rely on artificial, or "prosthetic," limbs to improve their quality of life. Prosthetic limbs have undergone significant research and development aimed at partially restoring motor and sensory capabilities to their users. Some existing prosthetic hand systems, for example, include individually movable fingers that can be configured to achieve certain common gripping patterns, e.g., controlled based on explicit user input (e.g., via buttons or voice control) or, in some cases, directly based on physiological signals from the user's brain, nerves, or muscles. Some systems also include sensor-based feedback mechanisms, e.g., to directly control the prosthetic device or mimic a sense of touch. Prosthetic devices with such advanced functionality typically include—in addition to the prosthetic components themselves (e.g., hands, fingers, joints, etc.)—motors, sensors, controllers, power supplies, electrical connectors, interfaces, and feedback mechanisms, as well as, in some cases, software. As a result, advanced prosthetic devices tend to be expensive not only to manufacture, but also to maintain and/or repair.

Prosthetic hands can break several times per year through accidents or normal wear-and-tear. If a major component or piece malfunctions or breaks, the prosthetic device may be rendered partially or completely useless, and must be replaced at significant cost and time. Presently, when a prosthetic device breaks, the user typically sends it back to the prosthetist who prescribed it. The prosthetist in turn, if unable to repair the device themselves, may send it back to the manufacturer. With conventional prosthetic device designs and constructions, which are limited to traditional manufacturing processes, the repair of the device may involve that each component (e.g., gear, bearing, linkage structure, etc.) is individually reconstructed and reinstalled, which generally requires a skilled craftsman, and is time-consuming and expensive. Sometimes, the overall process takes several months. In the interim, while the prosthetic hand undergoes repairs, the user may be left without a working or functioning limb, or with a replacement prosthetic hand which is an unfamiliar device for the amputee, both of which can severely reduce their quality of life for an uncertain amount of time.

SUMMARY

Described herein are prosthetic devices and systems, including "high-functioning" prosthetic devices and systems with motor and/or sensory functionality, that can be manufactured and/or repaired at lower cost and/or in reduced time, compared with many conventional designs, e.g., leveraging a modular design and/or recent improvements in materials and/or manufacturing processes. While this disclosure focuses, specifically, on prosthetic hands, some of the design principles and features described below more broadly apply to prosthetic limbs in general.

In some embodiments, a modular prosthetic limb includes multiple sub-assemblies, or "modules," that allow a defective module to be easily replaced or "swapped," increasing the overall life of the prosthetic limb and facilitating, in many cases, repair by the prosthetist or even the user themselves. For example, a prosthetic hand may include finger and/or thumb modules that are releasably attached to a palm module, allowing a broken prosthetic finger or thumb module to be detached from the palm module and a new finger or thumb module to be attached in its place. Simply swapping out a module of the prosthetic device at the assembly level (e.g., swapping an entire finger of a prosthetic hand instead of painstakingly replacing a single linkage cable in the finger) eliminates much of the time (and, thus, often also the cost) associated with the repair of conventional devices. Further, in situations where the user does not already have the replacement module on hand, the user may be able to take advantage of a partially functioning device (e.g., missing only the function of one defective finger) while waiting for the replacement module.

In some embodiments, an additive manufacturing technique, commonly referred to as three-dimensional (3D) printing (broadly understood), is used to cost-effectively manufacture one or more parts of a prosthetic device. 3D printing techniques have evolved to a point where they allow producing internal geometries that are impossible or very difficult to accomplish with traditional mold and/or machining processes. Leveraging this capability, prosthetic device design can be significantly simplified and/or consolidated, in accordance with some embodiments, by manufacturing (e.g., printing) a prosthetic device component with one or more functional parts, such as, e.g., gears, as a single, monolithic component. Thus, instead of, for example, mounting a separately manufactured gear on a structural prosthetic device component, the gear may be formed as an integral part of the component, inseparable from other portions of the component. Monolithic integration of structural and functional parts is herein also referred to as "functional integration."

In some embodiments, the disclosed prosthetic devices are provided with advanced motor and sensory functionality. Advanced motor functionality may be provided, for example, by equipping one or more modules of a modular prosthetic device (e.g., the finger modules in a prosthetic hand) with motors and associated position transducers (e.g., as provided in servomotors) that allow controlled movements of those modules relative to other modules, responsive to an electronic controller that operates on physiological signals, such as myoelectric signals, which are electrical signals manifesting neuromuscular activations associated with muscle contraction. A suitable algorithm (e.g., a trained machine-learning model), implemented in hardware and/or software, may be used to map the myoelectric or other physiological signals to the motor input signals. Sensory functionality is provided, in some examples, by force sensors incorporated into the prosthetic device (e.g., in the fingertips of a prosthetic hand) to measure external forces exerted on the device (e.g., forces acting on the fingertips when the prosthetic hand grips an object). The strength of the measured forces may be communicated to the user, e.g., visually or haptically.

In accordance with one aspect, a modular prosthetic hand includes a palm module, a plurality of finger modules each including a knuckle section releasably attached to the palm module, and in some examples a thumb module including a metacarpal section releasably attached to the palm module. The modular prosthetic may further include a wrist module with an electric quick disconnect (EQD) coupling mechanism for connection to a prosthetic socket. The wrist module may be releasably attached to a mounting recess within the palm module.

The palm module defines a plurality of knuckle cradles, and the knuckle sections of the finger modules are releasably attached to the palm module within corresponding knuckle cradles. A surface portion of each knuckle cradle geometrically conforms to a mating surface portion of the corresponding knuckle section, and movement of the knuckle section relative to the palm module is fully constrained by a configuration of the mating surface portions of the knuckle cradle and the corresponding knuckle section. For example, the relative movement may be constrained at least in part by an interlocking fit, a friction fit, or a snap fit between the mating surface portions. In some embodiments, the palm module includes a palmar plate and a dorsal plate separably affixed to each other (e.g., with screws). The palmar and dorsal plates together define the plurality of knuckle cradles. When the palmar and dorsal plates are separated, the knuckle sections of each of the plurality of finger modules can be removed from, or inserted into, a palmar or dorsal portion of the corresponding knuckle cradle in a direction normal to the plane of the palmar and dorsal plates.

The finger modules may each include, in addition to the knuckle section, a proximal phalanx and a distal phalanx. The proximal phalanx is attached to the knuckle section by a rotary hinge joint. The knuckle section includes an actuation mechanism and associated actuator motor configured to cause rotation of the proximal phalanx about the first rotary hinge joint. The distal phalanx may be attached to the proximal phalanx via a second rotary hinge joint. The proximal and distal phalanges may be configured in a double-rocker four-bar linkage, such that rotation of the proximal phalanx about the first rotary hinge joint causes a coordinated rotation of the distal phalanx about the second rotary hinge joint. The palm module may include electronic control circuitry to control the actuator motors of the finger modules. The finger modules may further include position transducers associated with the respective actuation mechanism (e.g., as part of servomotors), along with electrical wiring for connecting the actuator motor and the position transducer to the electronic control circuitry. In some embodiments, one or more of the finger modules each include a force sensor to measure an external force acting on the finger module and electrical wiring for connecting the force sensor and the actuator motor to the electronic circuit. The force sensor may be placed at the tip of the distal phalanx of the respective finger module. The palm module may include a visual indicator (e.g., an LED indicator ring) configured to indicate the strength of the external force.

In accordance with another aspect, a modular prosthetic hand includes a palm module; a plurality of finger modules movably attached to the palm module; one or more force sensors (e.g., force-sensitive resistors) integrated into the palm module and/or the finger modules to measure one or more respective external forces acting on the palm module or the finger modules; and a visual indicator within the palm module, communicatively coupled to the one or more force sensors and configured to indicate a strength of the one or more external forces. The visual indicator may include a ring of LEDs, optionally including multiple sections having LEDs of different respective colors, configured to sequentially light up as the strength of the external forces increases from a set first strength to a set second strength. The visual indicator may be electrically connected to electronic control circuitry contained in the palm module, and communicatively coupled to the one or more force sensors via, the electronic control circuitry. In some embodiments, the finger modules are motorized and configurable to exert a grip, and multiple force sensors are placed to collectively measure a strength of the grip. The prosthetic hand may include an exterior layer of compliant material (mimicking skin), and the one or more force sensors may be placed underneath the exterior layer.

In accordance with yet another aspect, a prosthetic digit includes a first segment including a motorized first gear (e.g., a worm gear); and a second segment attached to the first segment by a rotary hinge joint and including a second gear that engages the first gear such that rotation of the first gear causes the second segment to rotate about the rotary hinge joint. The second gear is formed as an integral part of the second segment, inseparable from other portions of the second segment. In some embodiments, the prosthetic digit is a prosthetic finger whose first segment is a knuckle section and whose second segment is a proximal phalanx of the finger, the first gear being a worm gear. In other embodiments, the prosthetic digit is a prosthetic thumb whose first segment is a proximal phalanx and whose second segment is a metacarpal of the thumb. The metacarpal may include an additional gear (i.e., a third gear of the prosthetic thumb), likewise forming an integral, inseparable part of the metacarpal, for engagement with a motorized gear of a palm module when the prosthetic thumb is movably attached to the palm module at a joint.

The foregoing summary introduces various design principles, features, and example embodiments of the disclosed subject matter, and is not intended to limit the scope of any claimed embodiment in any way. In particular, it is to be understood that the various disclosed features and design principles need not be applied together in a single embodiment. For example, the use of force sensors and visual indicators, or functional integration (e.g., of 3D-printed gears) are in no way contingent upon a modular design of a prosthetic hand.

BRIEF DESCRIPTION OF THE DRAWINGS

The accompanying drawings, which are incorporated in and constitute a part of this specification, illustrate example embodiments of the present disclosure and, together with the description, serve to explain the principles of the disclosure.

DETAILED DESCRIPTION

Figure 1:
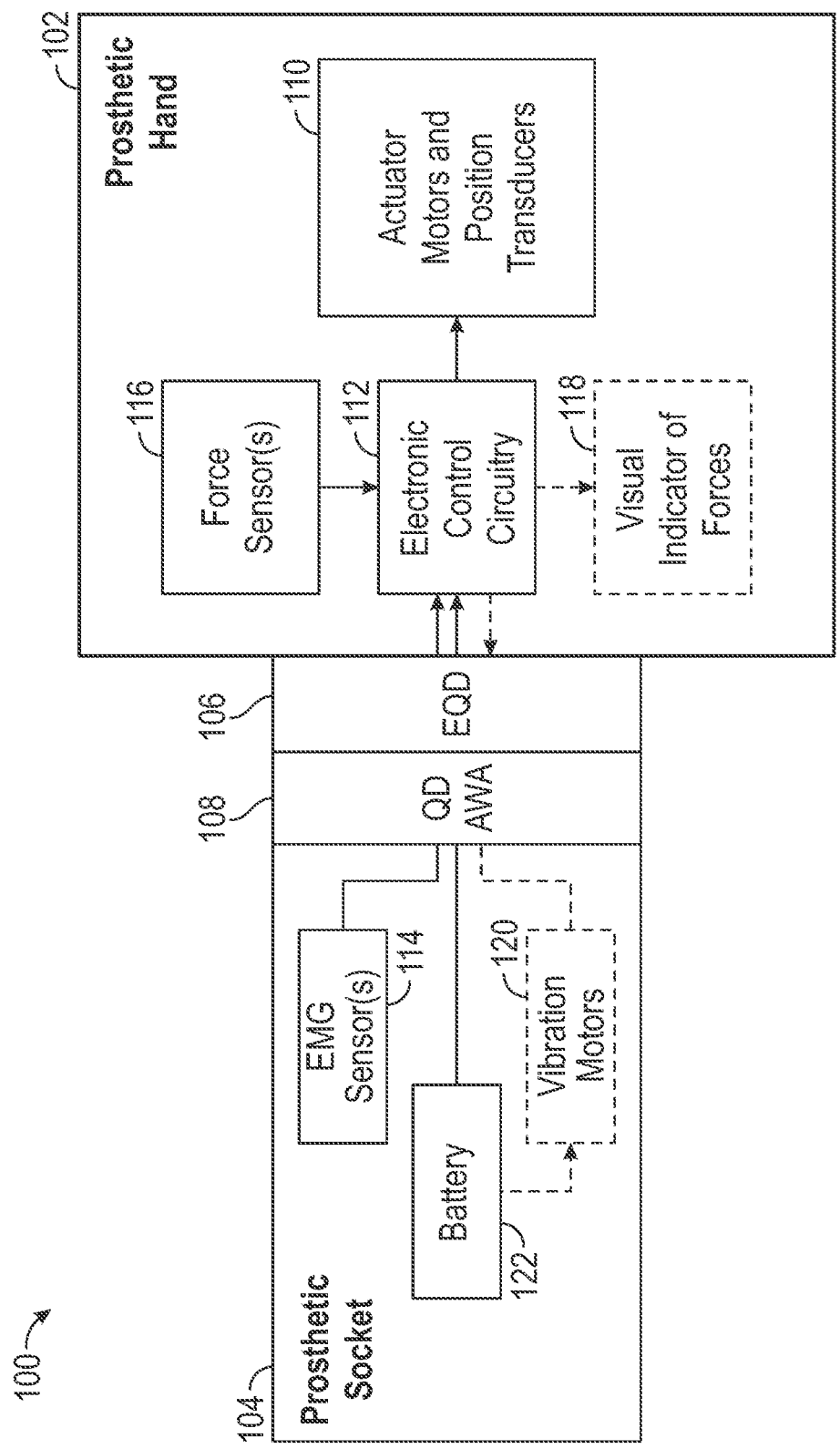
FIG. 1 is a block diagram of an example bionic hand system.

The present disclosure is generally drawn to prosthetic limb devices and systems. Such systems are commonly employed by amputees or persons with limb differences. However, apart from the field of prosthetics, the disclosed devices and systems may also find applications in other fields of technology, such as computer-human interaction or robotics. Any human recipient of a prosthetic device (whether or not that recipient has an amputation or limb difference) is herein also referred to as a "user." Embodiments of disclosed prosthetic devices and systems include, but are not limited to, "bionic" devices and systems. The term "bionic" is herein used with references to a prosthetic device or system that connects to the user's nerves, brain, or muscles.

In the following, an example prosthetic hand device and system are described with reference to the accompanying drawings. Numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well known structures are not described in detail in order to not obscure some of the aspects and/or features described or referenced herein.

In the following description, the nomenclature of human anatomy is employed with reference to the prosthetic hand. That is, components of the prosthetic device that serve as substitutes for or mimic certain anatomical parts of the hand, such as, e.g., the palm, fingers, thumb, wrist, knuckles, metacarpals, or phalanges of the fingers and thumb, will generally be referred to by these anatomical terms. Further, the terms "proximal" and "distal" will be used consistently with anatomical nomenclature, indicating parts or sites closer to or farther away from the relevant point of reference, respectively. For example, when referencing phalanges of the fingers, the phalanx closer to the palm or wrist (serving as the relevant reference point) is the proximal phalanx, and the phalanx farther away from the palm or wrist is the distal phalanx. As another example, on a prosthetic socket worn around the user's forearm or stump, the distal end is the end to which the prosthetic hand will attach. As will be readily appreciated, not every anatomical part necessarily has a counterpart in the prosthetic device, and vice versa. For example, while a human second to fifth fingers or digits (i.e., index finger, middle finger, ring finger, and little finger) each include proximal, middle, and distal phalanges, a prosthetic finger in accordance with various embodiments includes only two segments, one corresponding to the proximal phalanx and one corresponding to the combination of middle and distal phalanges. Similarly, while a human thumb includes proximal and distal phalanges, a prosthetic thumb in accordance with some embodiments includes only one segment corresponding to both phalanges.

Turning now to the drawings, FIG. 1 is a block diagram of an example bionic prosthetic hand system 100, conceptually illustrating various functional components of the system 100 and their electrical connections. The system 100 includes a bionic prosthetic hand 102 and an associated prosthetic socket 104. The prosthetic socket 104 may take the form of a sleeve or similar structure into which an amputee or limb-different person can place their residual arm (also referred to as a "stump" or "residuum").

The prosthetic hand 102 may be mechanically attached and electrically connected to the socket 104 via a male-to-female EQD interface. In an example embodiment, the male component 106 of the interface may be an EQD coupling mechanism (or simply "EQD) located on the proximal end of the prosthetic hand 102, and the female component may be attached to the distal end, or embedded within a distal portion, of the prosthetic socket 104. The female, receiving component 108 may be a QDAWA, and may come in the form of a four pin or six pin connection. The male EQD 106 may be easily attached or mounted to the QDAWA 108 via a coaxial plug affixed to the QDAWA 108 that is received by a 4 or 6 pin receiving slot within the EQD 106. In an exemplary embodiment, these connections are how signals and/or power are sent from or to peripheral components located in the prosthetic socket. The EQD interface allows the prosthetic hand 102 to be quickly and easily attached to, removed from, and re-attached to the prosthetic socket 104.

The prosthetic hand 102 includes actuator motors 110 and associated actuation mechanisms to move one or more prosthetic digits (e.g., thumb and second to fifth fingers) relative to a palm module of the hand. For example, as illustrated in more detail below, each of the second to fifth prosthetic fingers may have an associated motor causing one-dimensional rotation to implement flexion and extension of that finger, while the prosthetic thumb may have two associated motors and actuation mechanisms to allow for two-dimensional thumb movements. The actuator motors 110 may be located in the fingers, the palm module, or some combination of both. The prosthetic hand 102 further includes electronic control circuitry 112, e.g., located in the palm module, that provides control signals and power to the actuator motors 110. In various embodiments, the electronic control circuitry 112 is implemented on a printed circuit board (PCB) that includes one or more processors as well as memory storing software for execution by the processor(s). The actuator motors 110 may have associated position transducers, i.e., sensors providing position feedback, for precise control of finger configurations. For example, the actuator motors 110 may be servomotors, which implement closed-loop control with integrated position transducers. Alternatively, position transducers may be provided separately from the motors 110, and position feedback may be provided via the electronic control circuitry 112. The electronic control circuitry 112 may execute a program, implemented in hardware and/or software, to configure the prosthetic digits, using the motors 110, to mimic operation of a human hand. For example, the prosthetic hand 102 may be configured for various grip patterns. Six common grip patterns familiar to those skilled in the art include power grip, key grip, three jaw chuck, tool grip, hook grip, and fine pinch. However, the disclosed prosthetic systems may, in some embodiments, also support different or additional grip patterns and hand configurations.

The prosthetic socket 104 includes one or more myoelectric, or "electromyographic" (EMG), sensors 114, e.g., implemented by surface electrodes located at the interior of the socket sleeve for placement in contact with the user's skin, that measure electrical signals (e.g., electrical currents or voltages) that are generated in muscles during their contraction, representing neuromuscular activities. These EMG sensors 114 allow a user, such as an amputee, to activate grip patterns myoelectrically by flexing the skeletal muscles of their arm. In some embodiments, the grip pattern is selected using buttons, a touch screen, or some other explicit external user input, while the actuation of the selected pattern is accomplished myoelectrically with a single channel of control. In more advanced control schemes, multiple EMG sensors 114 may be used to provide multiple myoelectric channels of control, and the combination of control signals on those channels may be mapped onto the grip patterns. For instance, in one example, the combination of EMG signals from two EMG sensors 114 is mapped onto a set of six grip patterns. The mapping from two or more EMG signals to multiple grip patterns may be learned by a machine-learning model, and may be specific to the user. In this manner, the prosthetic hand can be controlled more intuitively, without relying on explicit grip pattern selection. In another example embodiment, myoelectric actuation of the prosthetic hand may be combined with computer-vision-based selection of a grip pattern, e.g., using a camera installed on the prosthetic hand in conjunction with pattern-recognition software (e.g., executed on the PCB) trained to recognize objects; the appropriate grip pattern is selected based on the recognized object. Yet another embodiment provides intuitive control by utilizing a network of surgically innervated muscle tissue transplants as biologic signal operational amplifiers to drive all the degrees of freedom of the hand arbitrarily.

The prosthetic hand 102 may, as shown, include one or more force sensors 116 (e.g., force sensitive-resistors, micro-force transducers that measure forces piezo-electrically, etc.) to measure external forces applied to the hand 102. Such force sensors 116 may be embedded in the distal phalanges, e.g., at the fingertips, of one or more of the prosthetic fingers. In one example, the index finger and/or the middle finger of the prosthetic hand 102 are equipped with force sensors. Alternatively or additionally, force sensors 116 (e.g., five or more sensors) may be embedded in the palm module of the prosthetic hand 102. The force sensors 116 in the palm and/or fingers may be placed and arranged to collectively measure, when the palm and/or fingers are in contact with external objects during a grip, the strength of that grip.

The force sensors may be electrically connected to the electronic control circuit 112. The electrical output signals of force sensors in the distal phalanges of the fingers, for example, may be routed back to the electronic control circuitry through the fingers and part of the palm of the prosthetic hand via wires or other conductors. The electronic control circuitry 112, in turn, may relay the measured force signals from the environment to the user of the prosthetic hand system 100 via some feedback mechanism, e.g., visual or haptic feedback, as explained below. In this manner, interaction between the user of the prosthetic hand 102 and their environment can be improved. For example, if the user can see or feel how hard they are pressing on something, they may be able to adjust their grip force accordingly (via flexion of the arm muscles, as detected by EMG sensors). Without any type of feedback, the user would have no idea how hard to press or grip. This unknown is potentially hazardous for both human users and any fragile objects (e.g., glass, electronics, etc.) they interact with.

In some embodiments, feedback to the user is provided visually, e.g., via an electronic display, set of LEDs, or other visual indicators 118 incorporated into the prosthetic hand 102 or, alternatively, the prosthetic socket 104. In one example, the prosthetic hand 102 includes an LED indicator ring that lights up in a manner indicative of the strength of the force applied to the fingers or palm.

In some embodiments, feedback to the user is provided haptically, e.g., via one or more vibration motors 120 embedded within the prosthetic socket 104 at locations that allow the user to directly feel the vibrations (e.g. an arm stump) to which the prosthetic hand 102 is connected). During operation of the prosthetic system 100, as the user interacts via the prosthetic hand 102 with the environment such that locations of the hand 102 where the force sensor(s) are placed come into physical contact with objects in the environment, the resulting forces applied on the force sensors may be mapped proportionally to the output strength of the vibration motor(s) embedded within a prosthetic socket 104. For example, if the user is pressing down on a hard surface or object with the fingertip of the prosthetic hand 102, the user may be able to feel how hard they are pressing via a vibration in their socket. As another example, if another person or an object comes in contact with the palm (e.g., during a handshake, picking up of an object, or some similar motion), a proportional response may be sent to the user of the prosthetic hand 102 via the vibration motors in the prosthetic socket 104. In this manner, the force sensors operating in conjunction with the vibration motors can restore a (pseudo) sense of touch.

The prosthetic system 100 may utilize one or more power sources, located in the socket 104 and/or the prosthetic hand 102, to power various components of the system 100, such as the actuator motors 110, electronic control circuitry 112, force sensors 116, visual indicator(s) 118, and/or vibration motor(s) 120. In an example, as shown, the power source 122 is a battery in the prosthetic socket 104, which connects to the electronic control circuitry 112 (and via the control circuitry 112 to the motors 110 and visual indicator 118) in the prosthetic hand 102 via the EQD interface. The battery may be, for instance, a rechargeable lithium ion battery in the 5V-22V range.

To deploy the prosthetic system 100, the user may install the prosthetic hand 102 while the hand is in an extended position before powering up the system 100. Upon powering up, the prosthetic hand 102 may remain in a relaxed and open position while the processors onboard the PCB (or some other electronic control circuitry 112) begin their operational startup sequences. These sequences may comprise the loading of preprogrammed software that includes standard grip patterns, checking battery levels, ensuring successful connections and communications with all peripheral components (e.g., actuator motors, force sensors, vibration motors) and then displaying the status via an LED that may be present on the back of the prosthetic hand 102. After the PCB finishes its powerup sequence, pre-programmed software on the PCB may then allow the user to achieve, e.g., six common and distinct grip patterns, or any variation of customized grip patterns a user has programmed into their prosthetic hand, which may be activated by myoelectric detection of flexions of the user's skeletal muscles.

Figure 2A:
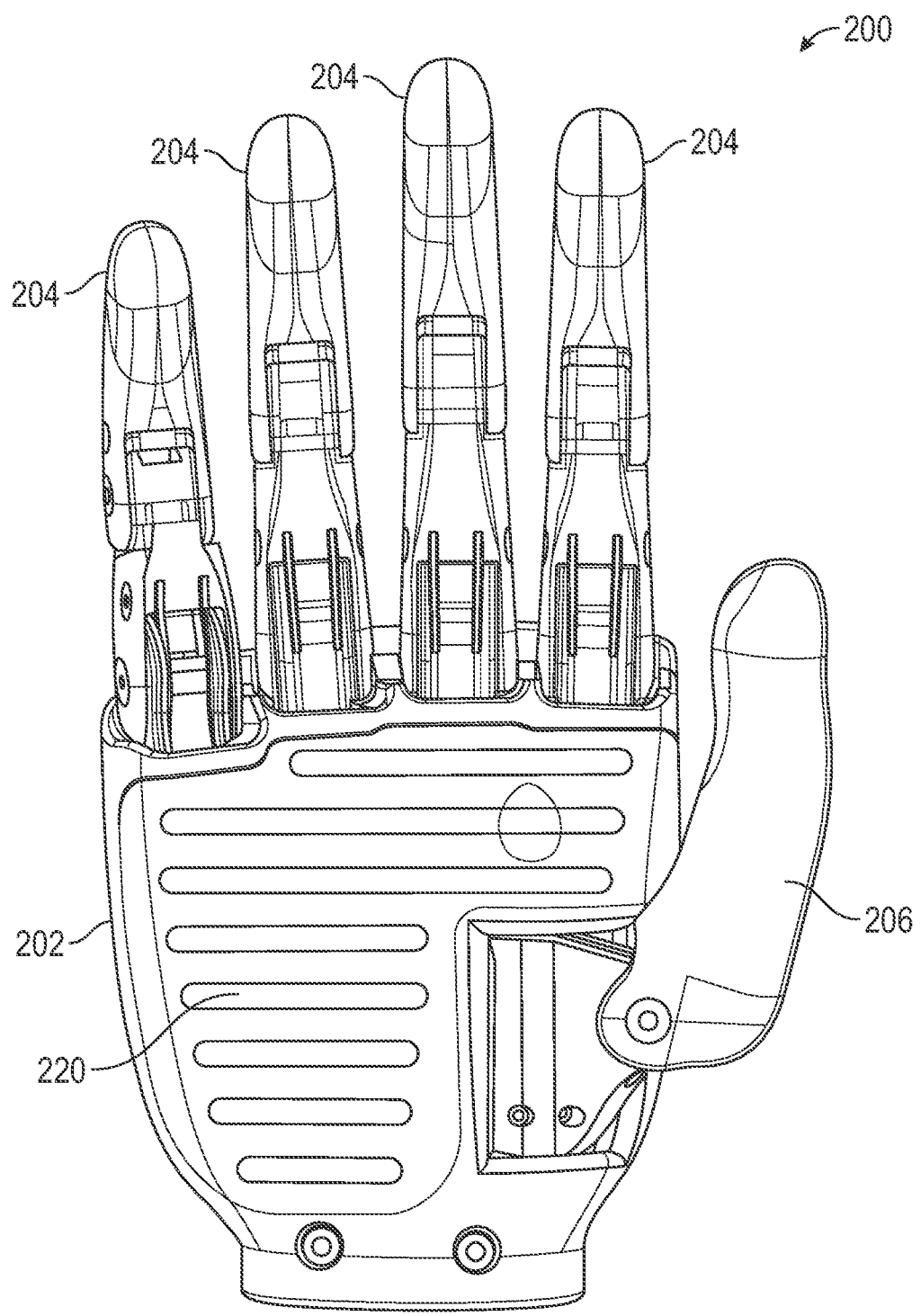
FIGS. 2A-2C are various views of an example modular prosthetic hand.
Figure 2B:
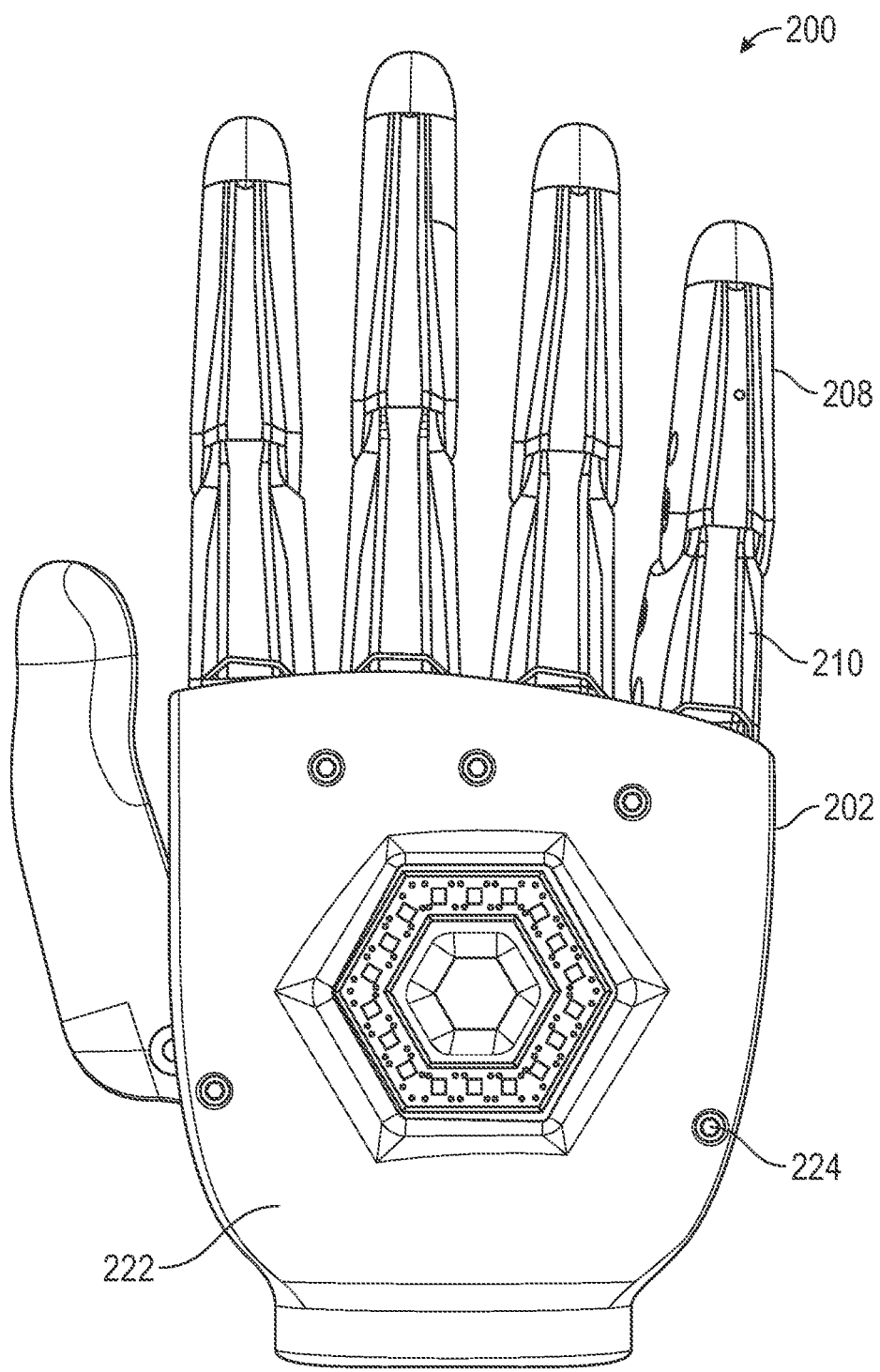
Figure 2C:
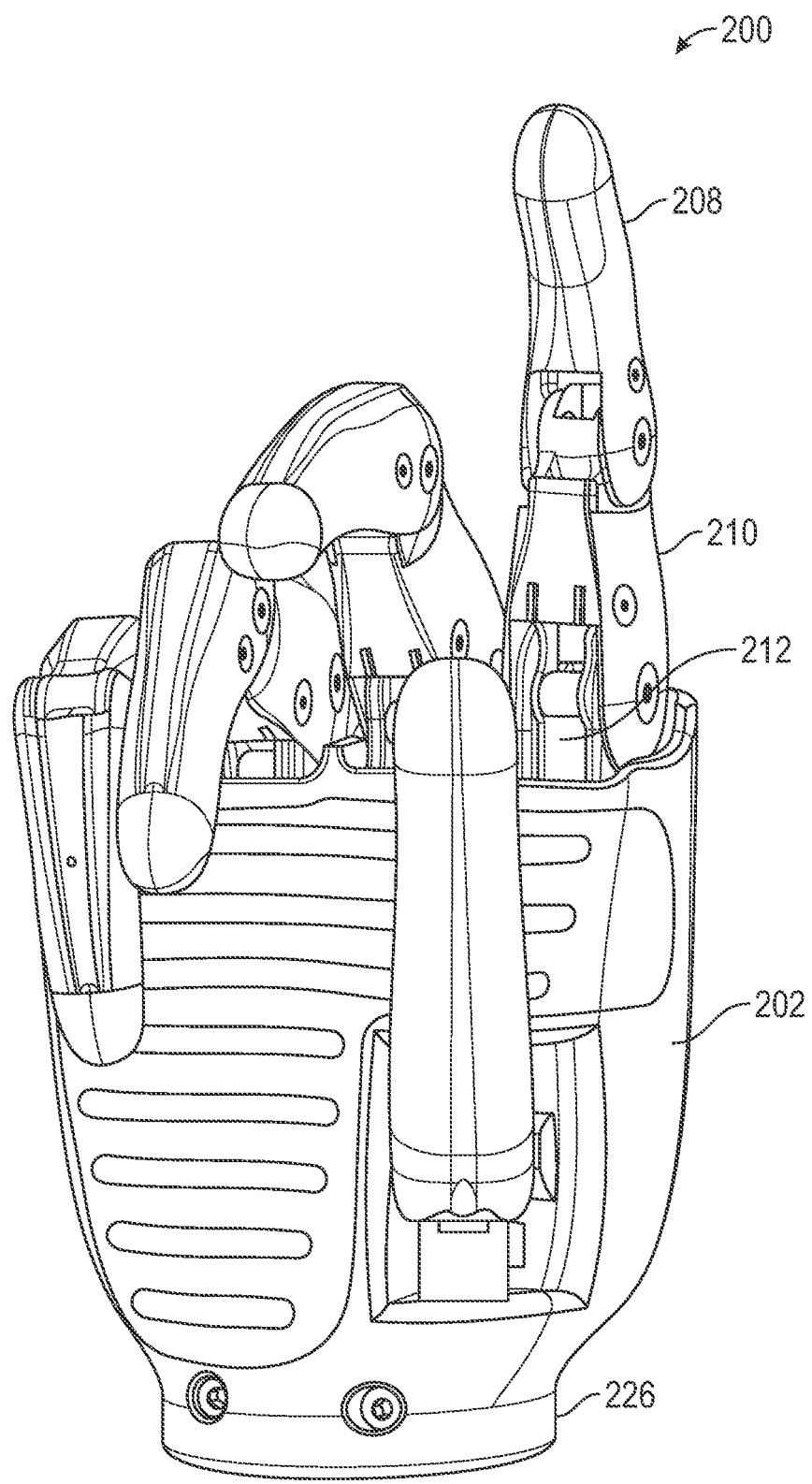

FIGS. 2A-2C illustrate, in various perspective views, an example modular prosthetic hand 200. The prosthetic hand 200 may be used in the bionic prosthetic system 100, and may be controlled based on myoelectric inputs, but can also be deployed in different systems and without myoelectric control. The prosthetic hand 200 includes a palm module 202, four finger modules (or simply "fingers") 204 corresponding to the second to fifth digits, and a thumb module (or simply "thumb") 206. The hand 200 may also include a wrist module (not shown in FIGS. 2A-2C) for attachment and electrical connection to a prosthetic socket. The four finger modules 204 may be completely assembled, pre-fabricated units that are modularly and/or interchangeably attached to the palm module 202. The thumb module 206 is mounted to the palm module 202 in a manner that renders it modular and interchangeable in some, but not all, embodiments. The modular design of the prosthetic hand 200 allows for easy repair when a finger module 204 (or, if modular, the thumb module 206) breaks or malfunctions, as the defective module 204 or 206 can simply be swapped out for a functioning one, as explained in more detail below.

The finger modules 204 as well as the thumb module 206 may be sub-assemblies of multiple segments attached to each other by joints (e.g., rotary hinged joints) that allow for relative movements between the segments. The segments generally include one or more phalanges and a knuckle section or metacarpal at which the finger or thumb is attached to the palm module 202. In the depicted example, each finger module 204 includes a distal phalanx 208, a proximal phalanx 210, and a knuckle section 212. The proximal phalanx 210 can rotate about a hinged joint connecting it to the knuckle section 212, and the distal phalanx 208 can rotate about a hinged joint connecting it to the proximal phalanx 210. In alternative embodiments, each finger module may include three phalanges (corresponding to distal, middle, and proximal phalanges in the human anatomy) that can rotate relative to each other and the knuckle section. The thumb module 206 includes, in the depicted example, a single phalanx movably connected (e.g., likewise via a hinged joint) to a metacarpal section attached to or within the palm module 202. In other examples, the thumb module 206 may have two phalanges. Via rotations about the joints, the configuration of the fingers 204 and thumb 206 can be changed. FIGS. 2A and 2B show the prosthetic hand 200 in a relaxed position with extended fingers 204 and the thumb 206 to the side, with FIG. 2A depicting the palmar side and FIG. 2B depicting the dorsal side. FIG. 2C shows the prosthetic hand 200 in a grip configuration, with flexed fingers 204 and the thumb moved in front of the palm.

The palm module 202 may be formed as a "clam-shell" design, with a palmar plate 220 (shown in FIG. 2A) and a dorsal plate 222 (shown in FIG. 2B) seated over the palmar plate 220. The two plates 220, 222 may be joined together, e.g., by screws 224. The palmar and dorsal plates 220, 222 serve a variety of roles and functions, but primarily act as a housing for mechanical and/or electrical components, including connective wiring. In an example embodiment, the palmar and dorsal plates 220, 222 house a PCB (implementing the electronic control circuitry 112), and encase, at least partially, knuckle sections 212 of the finger modules 204 and one or more proximal components of the thumb module 206. The palmar and dorsal plates 220, 222 may also act as receivers of one or more force sensors or transducers to detect or measure outside mechanical stimuli (e.g., sense a mechanical load on a location of the palm module 202). A proximal section of the palm module 202 may serve as a wrist section 226 to receive a separate wrist module (shown in FIG. 4).

Figure 3A:
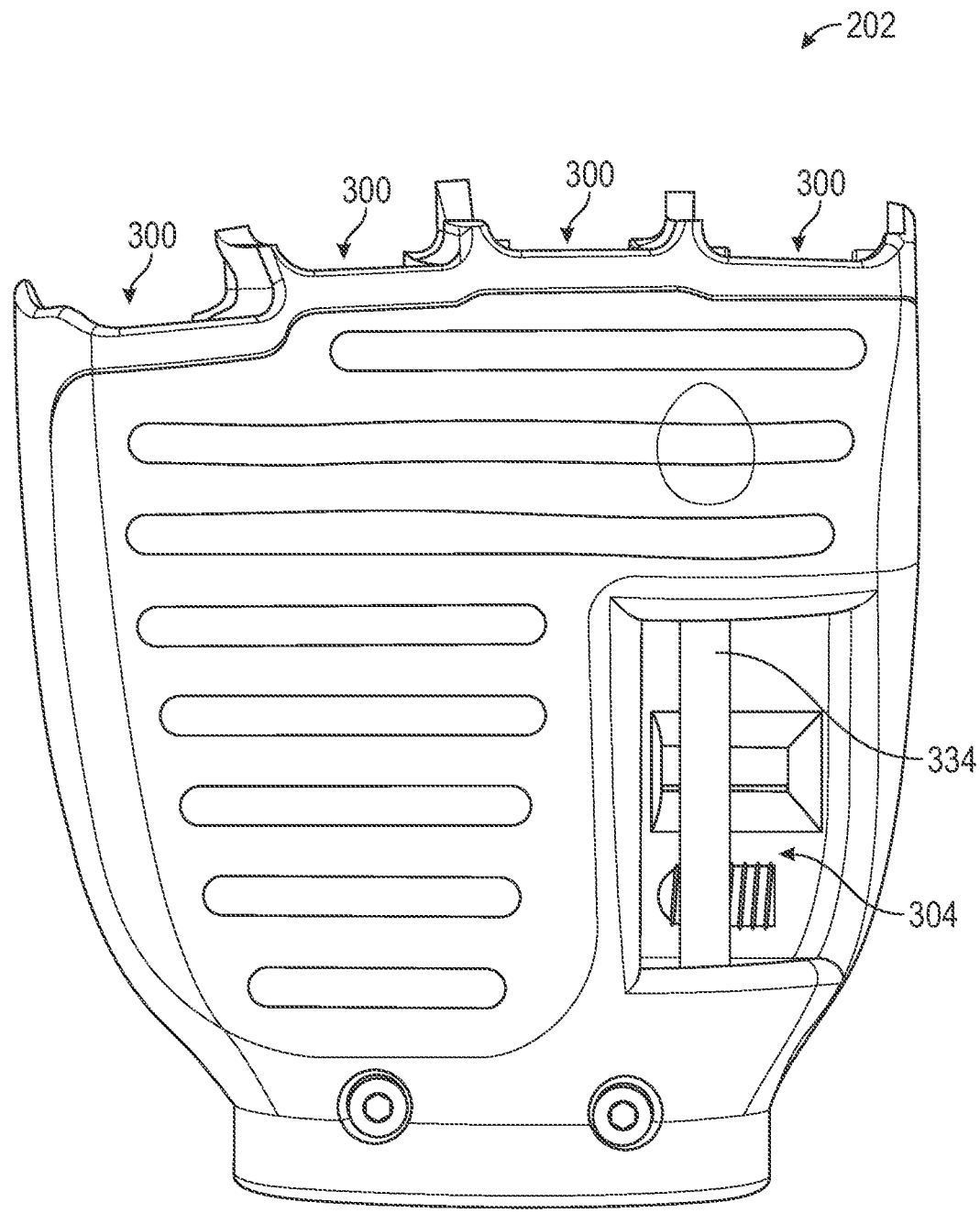
FIGS. 3A-3F are various views of portions of the example prosthetic hand of FIGS. 2A-2C, illustrating the attachment of finger and thumb modules to the palmar module.

FIGS. 3A-3F are various views of portions of the example prosthetic hand of FIGS. 2A-2C, illustrating the attachment of finger and thumb modules 204, 206 to the palmar module 202. FIG. 3A depicts the palmar module 202 by itself, with all finger modules 204 and thumb module 206 removed. As can be seen, the palmar module defines openings 300, 304 for each of the finger modules 204 as well as the thumb module 206. The openings 300 for the finger modules, herein also "knuckle cradles" or simply "cradles," are configured to receive and partially enclose the knuckle sections 212 of the finger modules 204 and secure them to the palm module 202. Similarly, the opening 304 for the thumb module is configured to receive and at least partially enclose the metacarpal 306 of the thumb 206, to which the phalanx 308 of the thumb 206 attaches. The knuckle cradles 300 and opening 304 for the thumb 206 may be formed integral with the palmar plate 220, the dorsal plate 222, or both. In the illustrated example, the knuckle cradles 300 have palmar and dorsal portions that extend from faces where the palmar and dorsal plates meet into the palmar and dorsal plates.

Figure 3B:
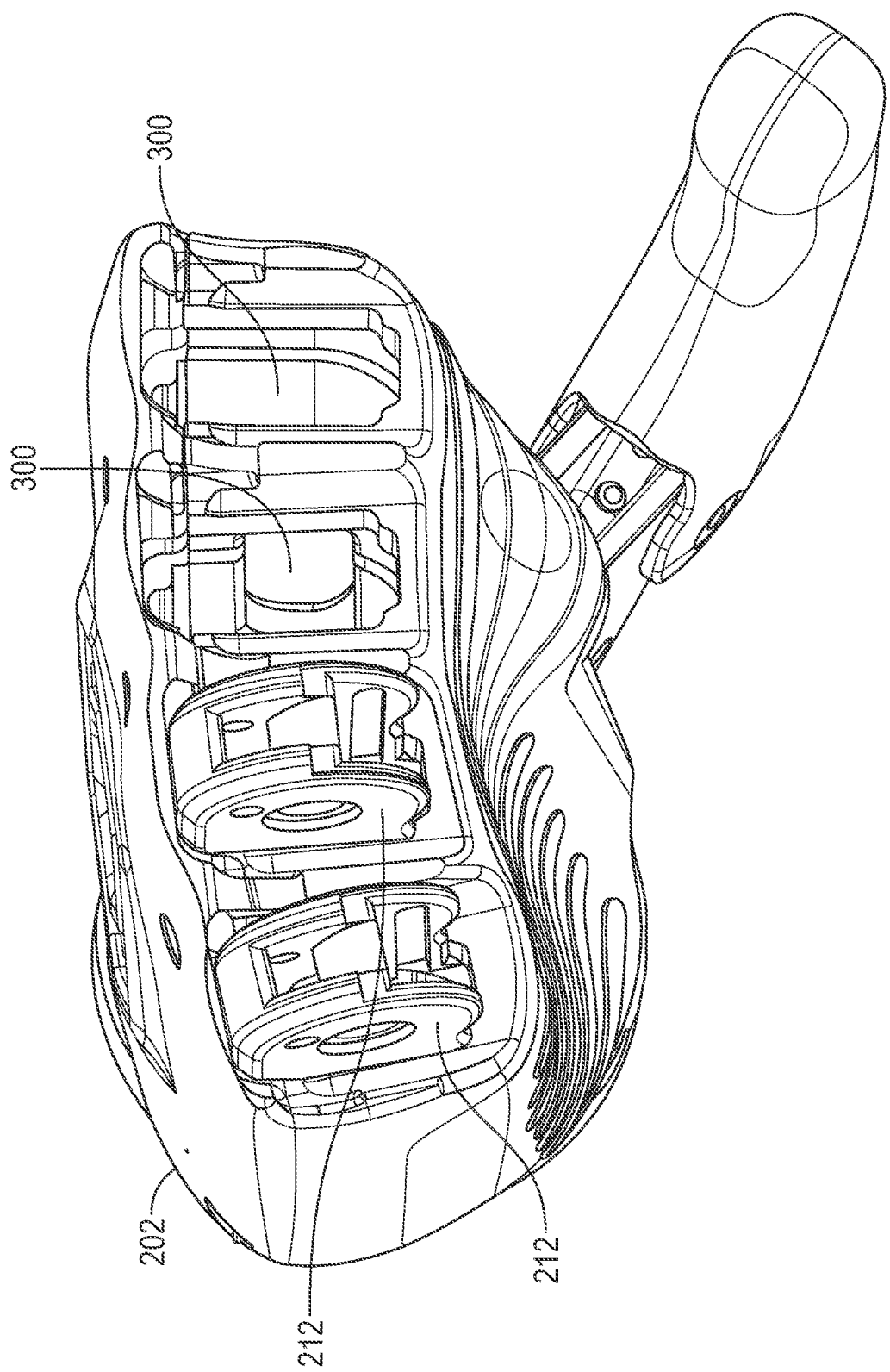

FIG. 3B shows the palm module 202 with knuckle sections 212 of the ring finger and pinkie inserted into their respective knuckle cradles 300. The phalanges of the ring finger and pinkie are not shown in FIG. 3B so as to not obstruct the view of the knuckle sections. It is to be understood, however, that in accordance with various embodiments, the finger module is attached as a whole when its knuckle section 212 is connected to the palmar module 202.

Figure 3C:
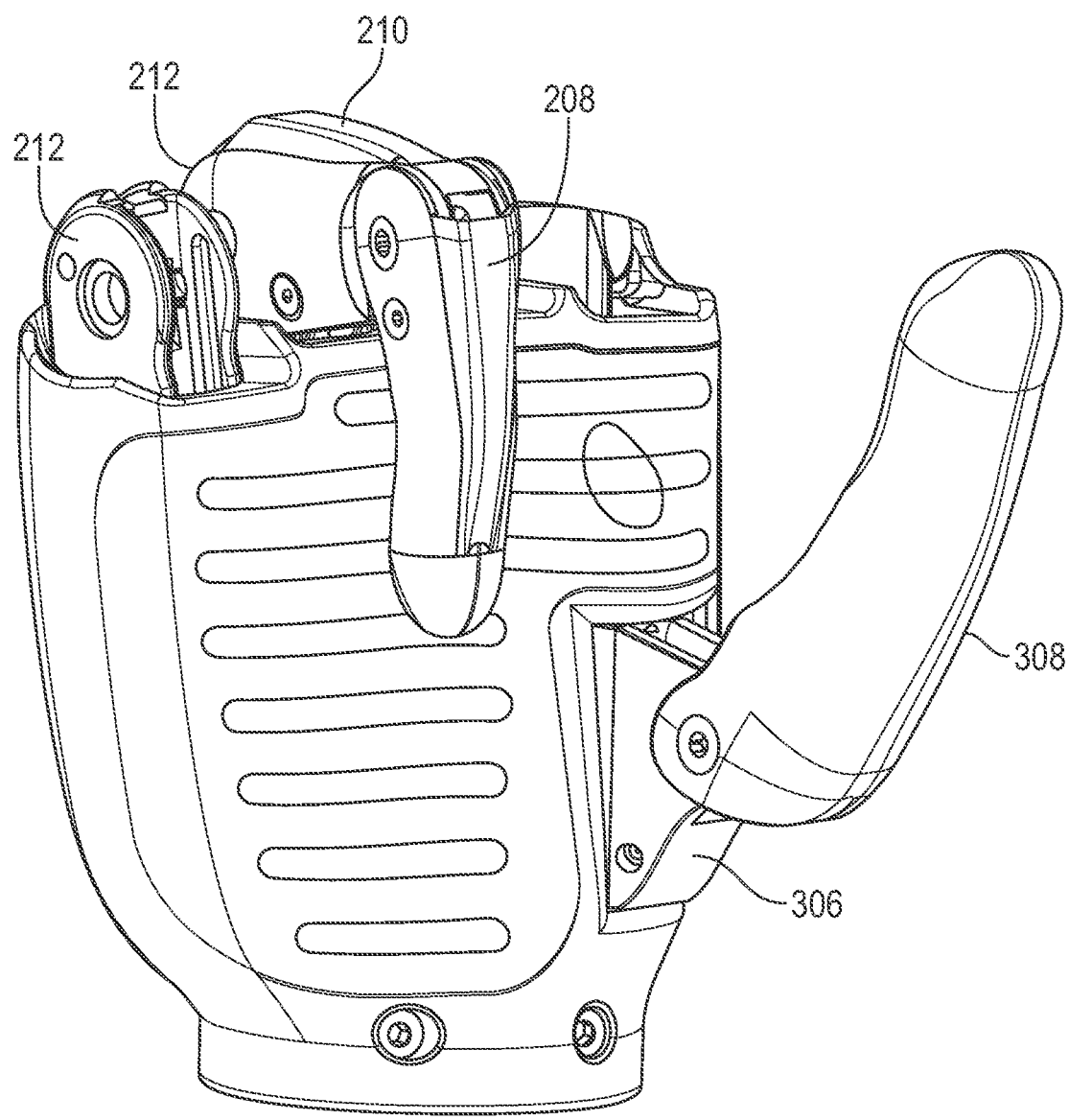

FIG. 3C shows the palmar module 202 with the ring finger attached. As illustrated, movement of the finger 204 relative to the palm module 202 is achieved via movement of the phalanges relative to the knuckle section 212, which itself is immovably attached to the palm module 202. To provide space for the finger movement about the fixed knuckle section 212, the knuckle section may protrude from the palm module 202. The depicted configuration, for example, allows for rotation of ninety degrees of the proximal phalanx 210 relative to the knuckle section 212. FIG. 3C also shows the metacarpal 306 of the thumb 206, which is received in the opening 304 of the palm module 202, and to which the phalanx 308 of the thumb 206 attaches.

Figure 3D:
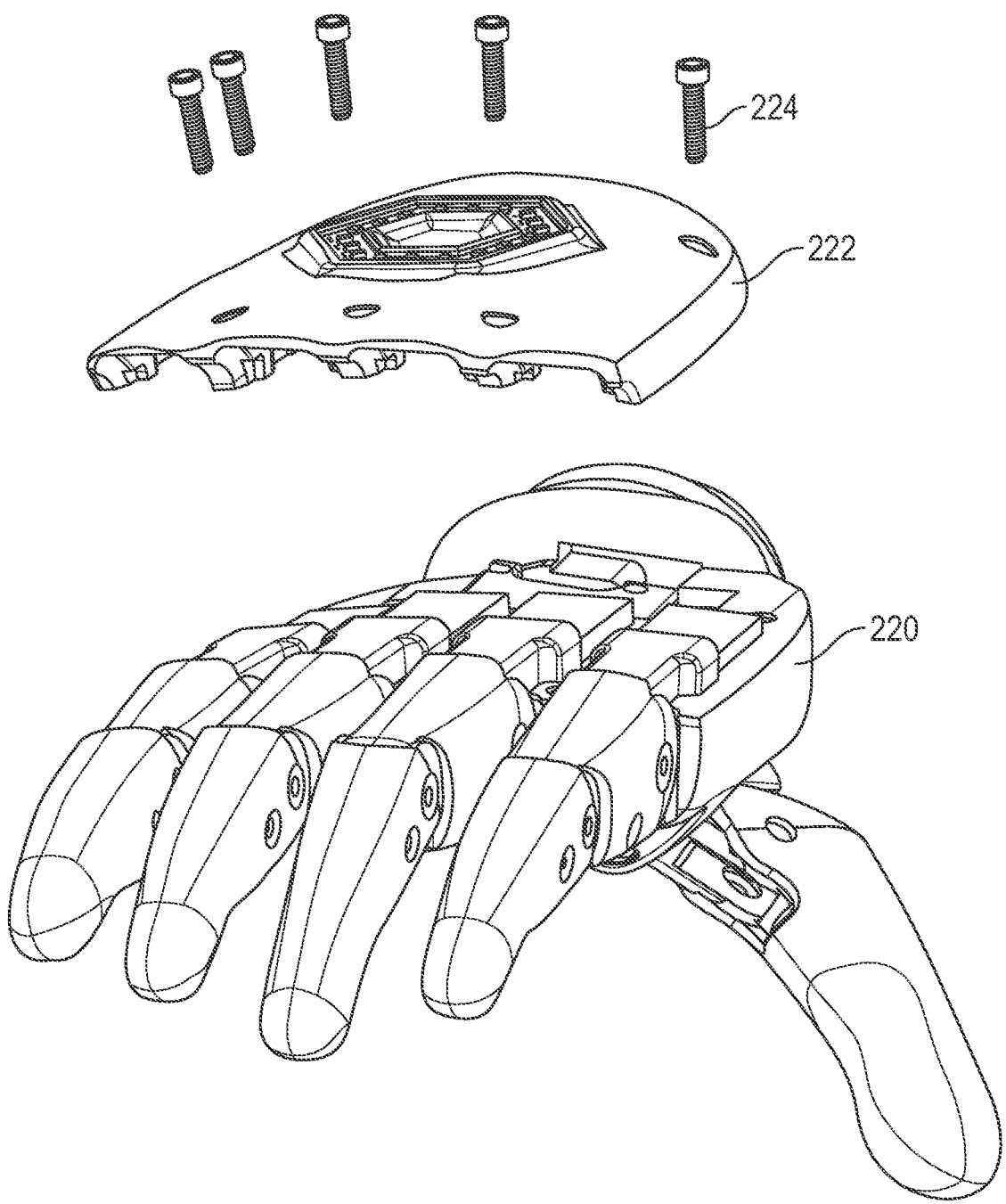
Figure 3E:
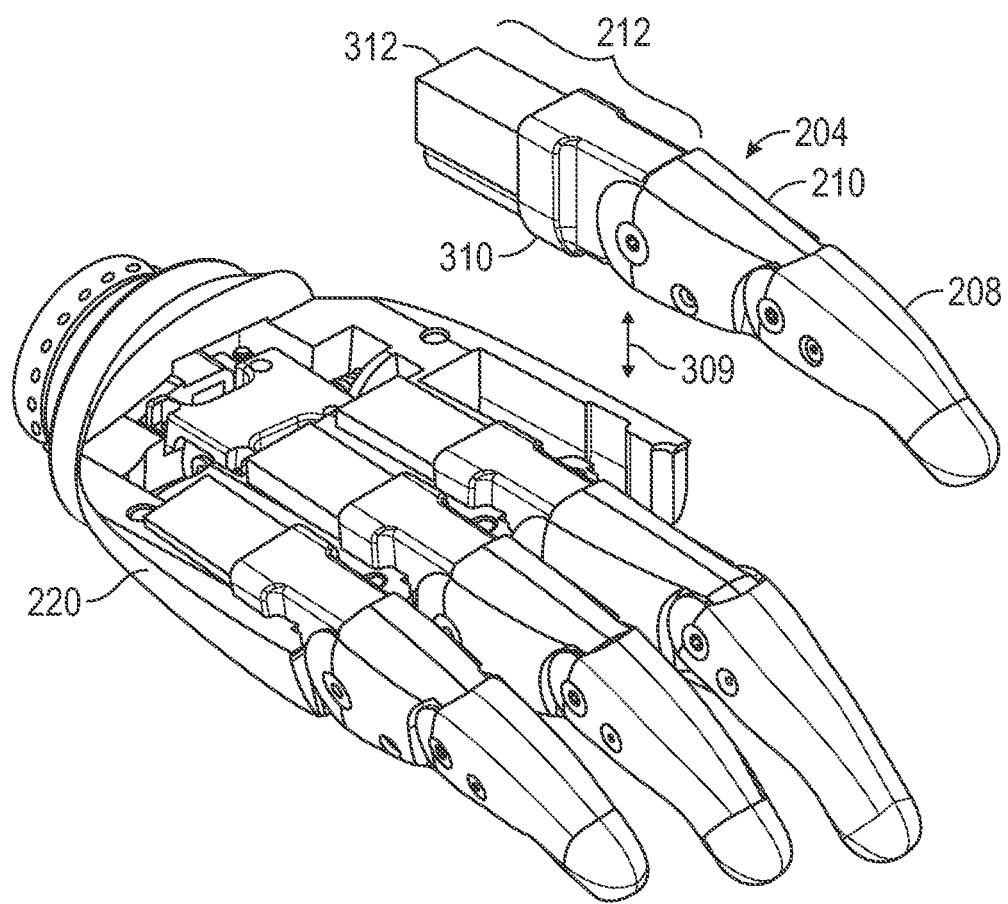
Figure 3F:
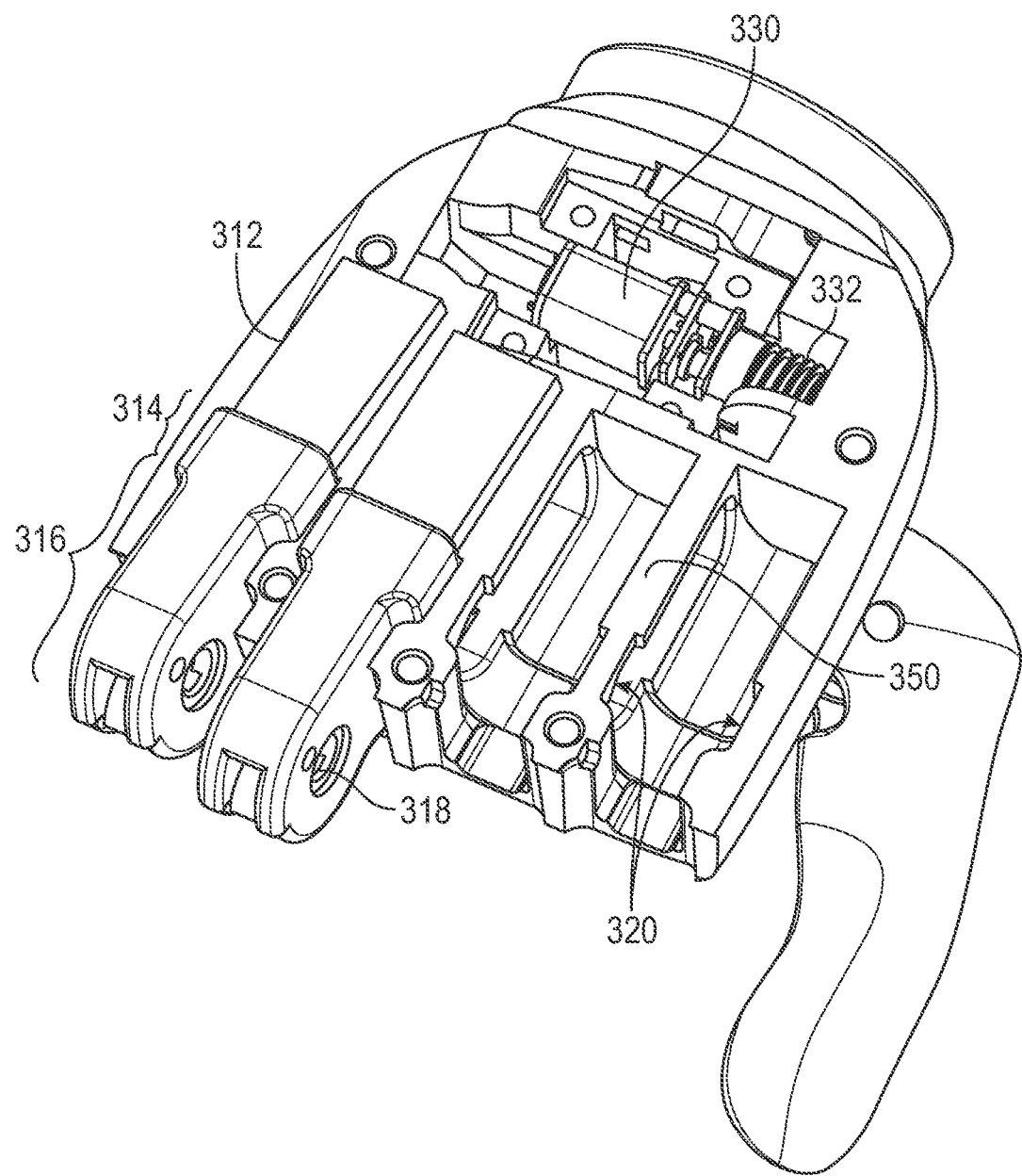

FIGS. 3D-3F show the palm module 202 with the dorsal plate 222 separated from the palmar plate 220. In this state, the finger modules 204 can be removed and inserted in a direction 309 normal to the plane of the palmar and dorsal plates 220, 222. For example, as depicted, the palmar portion of a knuckle cradle 300 may include bottom, side, and back walls that define a space into which the knuckle section 212 of the finger module 204 can be inserted from the top, as shown in FIG. 3E. Once the knuckle section 212 is seated within the palmar portion of the cradle 300, the dorsal plate 222 can be placed to cover the palmar plate 220 and knuckle section(s) 212 of the finger(s) 204, forming the top wall of the knuckle cradle. In alternative embodiments, the roles of palmar and dorsal plates in forming the knuckle cradle 300 may be reversed, that is, the knuckle cradles may be formed primarily in the dorsal plate, with the palmar plate providing the cover. Yet another possibility is to have palmar and dorsal plates define comparably sized portions of the knuckle cradles. In all these cases, the palmar and dorsal plates 220, 222 may be vertically fastened to each other, for instance, using screws or threaded inserts of some type. For example, screws or other fasteners 224 may be employed through the columnar structures 350 (labeled in FIG. 3F) separating adjacent cradles 300. Taking advantage of the preload force of the fasteners, the palmar and dorsal plates 220, 222 may act as a cradle and clamp to affix the knuckle section 212 relative to the palm module 202.

As shown in FIGS. 3E and 3F, the knuckle sections 212 of the finger modules 204 each include a knuckle housing 310 containing the actuation mechanism (e.g., linear actuators or gears) for the fingers, and a motor housing 312 encasing the associated actuator motor, which extends from the knuckle housing 310. The geometry of the knuckle cradles 300 may be designed to match the profile of the motor housing 312 and of an enclosed portion of the knuckle housing 310. Moreover, in various embodiments, the knuckle cradle 300 and knuckle section 212 have mating surface portions that are configured to fully constrain movement of the knuckle section 212 relative to the cradle 300, and thus relative to the palm module 202, obviating the need for any separate fasteners, such as screws, to affix the knuckle section 212 to the palm module 202. Instead, a finger module 204 can be installed, for example, by simply slotting the knuckle section 212 into the cradle 300, and connecting electrical wires, e.g., for the actuator motor and any force sensors embedded in the finger, to the PCB. Similarly, removing a finger module 204 involves disconnecting the electrical wires from the PCB, and pulling the finger vertically (in a direction normal to the palmar and dorsal plates) out of the cradle 300. In some embodiments, the PCB is housed in a recess of the dorsal plate 222.

FIG. 3F illustrates the mating surface portions in more detail. In the depicted example, the knuckle housing 310 has a wider proximal portion 314 and a narrower distal portion 316. When the knuckle section 212 is installed in the cradle 300, the distal portion 316 extends outside the cradle 300, providing room for connection of the proximal phalanx at a hinged joint formed in part by a bore 318 through the distal portion of the knuckle housing 310. The proximal portion 314 of the knuckle housing 310 has surface portions along the side, front, and back, that conform to mating interior surface portions of the cradle 300. More specifically, as shown, the cradle 300 includes a wider region formed by recesses 320 in the side walls that match the proximal portion 314 in both width and length. The proximal portion 314 of the knuckle housing fits within that recessed region, but is prevented from longitudinal movement (i.e., along a longitudinal axis of the finger 204 and cradle 300) in both directions by the narrowing of the cradle 300 both in front of and behind the recessed region. Thus, the finger 204 cannot be pulled out of the cradle 300 in the longitudinal direction. Lateral movement of the knuckle section 212 in the plane of the palmar plate 220 is, of course, precluded by the side walls of the cradle 300, and lateral movement of the knuckle section 212 normal to the plane of the palmar plate 220 is precluded by the bottom and top walls of the cradle 300 when the dorsal plate 222 is put on and affixed to the palmar plate. Thus, the cradle 300 blocks movement in all six directions. A configuration in which movement is constrained by blocking surfaces is herein also referred to as an "interlocking fit."

The depicted interlocking fit is just one nonlimiting example of a configuration that constrains relative movement between the knuckle section 212 and the palm module 202 without the need for separate fasteners. Another option to constrain movement is a snap fit. In a snap fit, which may be regarded a special case of an interlocking fit, at least one of the mating components is slightly deformable, and allows that component to be moved past an otherwise blocking surface with little force in one direction, but not the other. To implement a snap fit, the knuckle section may, for example, be configured with a small ledge or ridge that engages with a corresponding groove in the cradle (or vice versa) when the finger is pushed into the cradle, e.g., along a longitudinal direction, but that disengages only upon application of considerable force. With such a fit, it is possible to exchange finger modules without having to open the palm module. Yet another possibility is a tight friction fit, which constrains relative movement between the components by friction forces between the mating surface portions. In some embodiments, combinations of interlocking, snap, and/or friction fits acting along different directions may be used to fully constrain movement.

With renewed reference to FIG. 3F, the dorsal face of the palmar plate 220 may include a housing recess or housing port to receive a servomotor 330 and worm gear 332 for actuating the metacarpal section of the thumb module 206. This recess is contiguous with the opening 304 extending from the palmar face of the palmar plate 220, which receives the metacarpal section. The palmar plate 220 may contain a through hole for a shoulder bolt 334 extending through the opening 304 between the wrist and knuckle sides of the palmar plate 220, as shown in FIG. 3A. This shoulder bolt 334 will serve as the rotary axis for the hollowed out metacarpal section of the thumb module 206. In an example embodiment, small tabs matching the profiles of the servomotor 330 and worm gear 332 may be fastened to a top of the servo motor and the worm to clamp them down into their respective cradles within the palmar plate 220.

Figure 4:
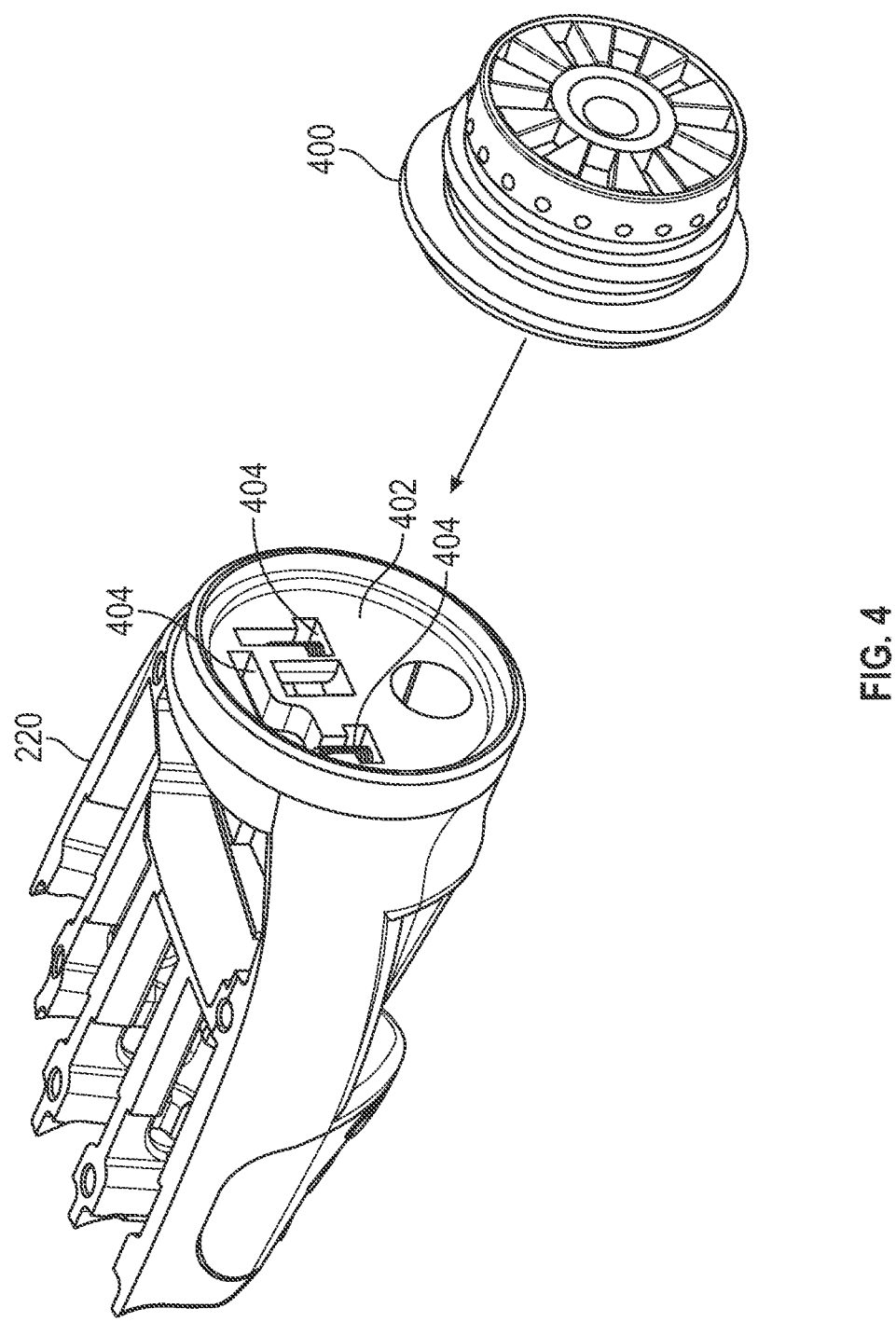
FIG. 4 is a perspective view of an example wrist module and corresponding portion of the palmar module of the example prosthetic hand of FIGS. 2A-2C.

FIG. 4 is a perspective view of an example wrist module 400 and corresponding portion of the palmar module 202 of the example prosthetic hand 200 of FIGS. 2A-2C. The wrist module 400 has an EQD coupling mechanism for connection to a corresponding female component (e.g., QDAWA) provided at the distal end of the prosthetic socket. In some embodiments, the wrist module 400 is an EQD wrist attachment of industry-standard variety; in other embodiments, it is customized to best accommodate the particular embodiment of the prosthetic hand 200 or terminal end of a separate prosthetic socket or receiving end (arm, limb, appendage, etc.) of a humanoid or general-purpose robot. The wrist module 400 may be mechanically and/or electronically connected to a proximally facing plate 402, including mounting recesses 404, of the wrist section 226 of the palmar module 200. Once coupled to the proximally facing plate 402 of the wrist section 226, the wrist module may be screwed in place. In this embodiment, the EQD coupling mechanism is modular in that, once the set screws are removed, it can be swapped out for a new wrist module. If such modularity is not desired, alternatively to providing the EQD coupling mechanism in a wrist module 400 separate from the palm module 202, the EQD coupling mechanism may be formed integrally with the palm module 202.

Figure 5A:
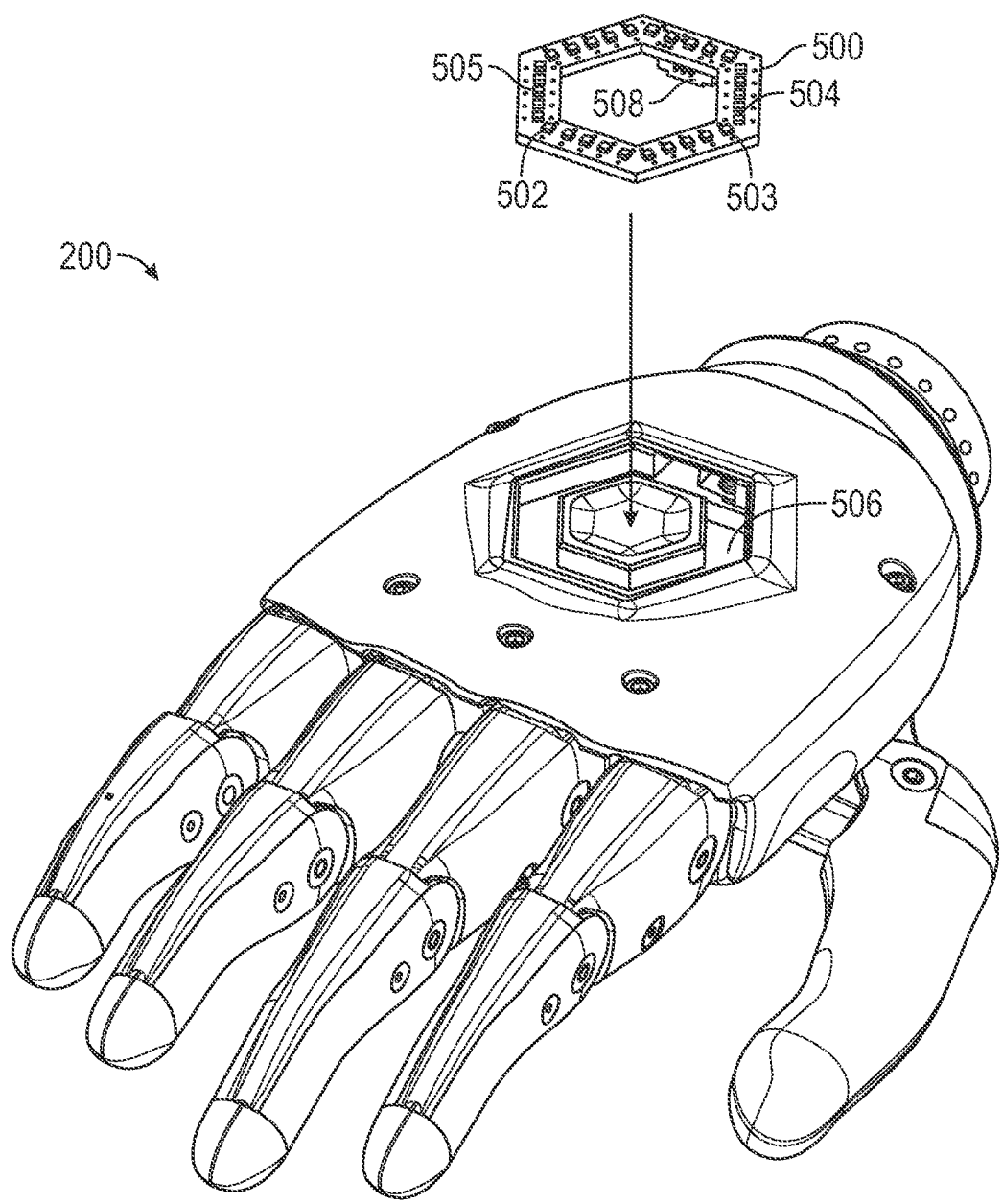
FIGS. 5A and 5B are views of the example modular prosthetic hand of FIGS. 2A-2C, illustrating an LED indicator ring as an example of a means for visually relaying force sensor measurements to the user.
Figure 5B:
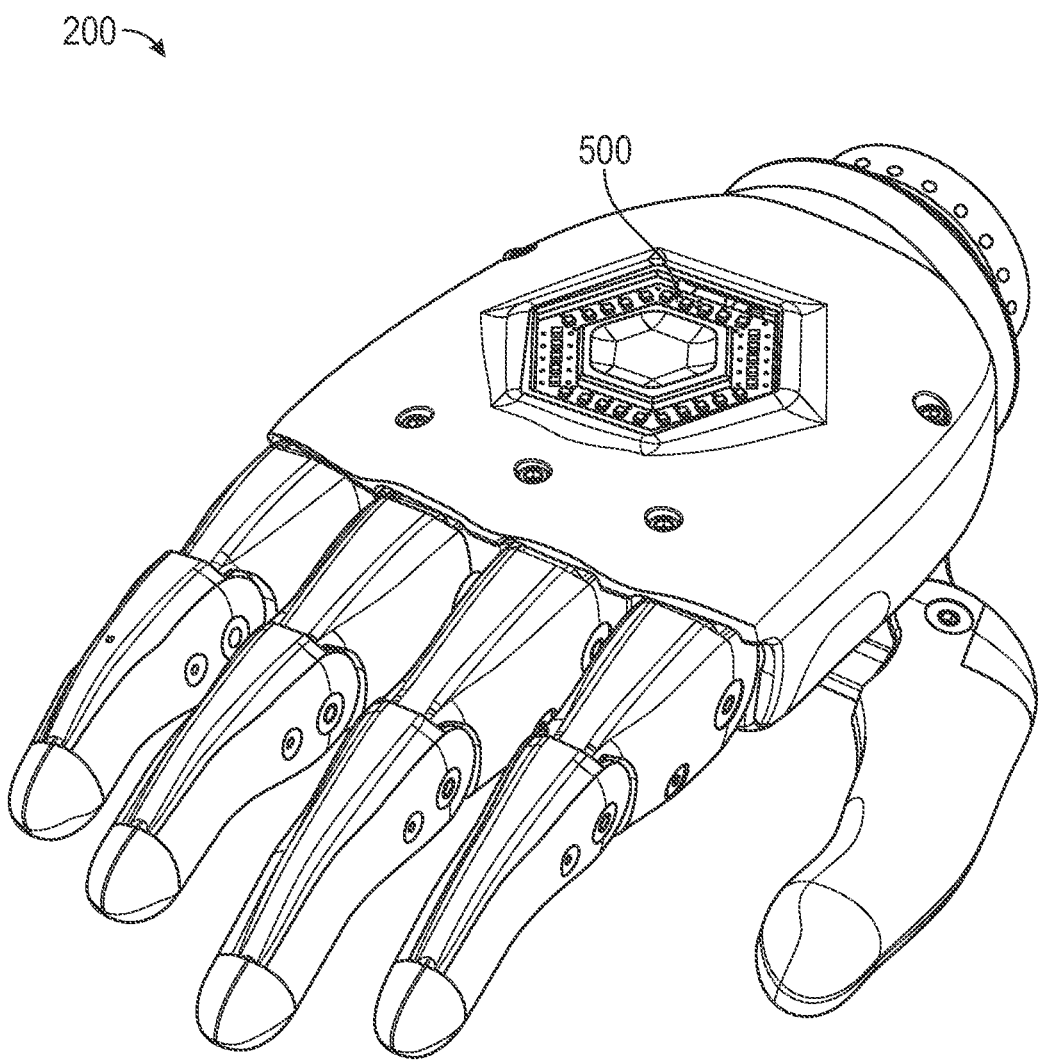

FIGS. 5A and 5B are views of the example modular prosthetic hand 200 of FIGS. 2A-2C, illustrating an LED indicator ring 500 as an example of a means for visually relaying force sensor measurements to the user. As shown, the indicator ring 500 includes LEDs 502, 503, 504 in a closed geometric arrangement, e.g., along the edges of a hexagon. Of course, other closed shapes (e.g., circles, triangles, etc.) as well as open arrangements along straight or curved lines are equally possible. The LEDs 502, 503, 504 are mounted on a suitable structural support. The indicator ring 500 may be mounted on the back of the prosthetic hand 200, i.e., on the dorsal face of the dorsal plate 222, such that it is easily viewable by the user during most typical grip configurations. For example, as shown in FIG. 5A, the dorsal plate 222 may include a recess 506 in the shape of the indicator ring 500, into which the ring 500 (or other arrangement of LEDs) may be inserted, resulting in the configuration shown in FIG. 5B.

The indicator ring 500 is electrically connected to the electronic control circuitry 112, which may provide both power and control signals for the LEDs. In some embodiments, the dorsal plate 222 houses a PCB implementing the control circuitry 112, and the indicator ring 500 is situated directly above the PCB and connected to it, e.g., via a connector block 508 extending from the underside of the ring 500. The LEDs are electrically configured to turn on in sequence as the magnitude of a control signal gradually increases from a lower threshold value to an upper threshold value. Accordingly, one of the LEDs is the first LED 503, which lights up as the control signal magnitude just barely exceeds the lower threshold value, and the additional LEDs along the ring light up sequentially along the ring as the signal magnitude grows, until the last LED 504 of the ring is reached when the signal magnitude is at the upper threshold value. The number of LEDs lit at a given time, thus, indicates the strength of the control signal. In accordance herewith, the control signal is generated based on force measurements with one or more force sensors, and increases monotonically with the strength of the measured external force, that is, the magnitude of the force sensor output signal for an individual sensor, or in the case of multiple force sensors, some combination of their force sensor output signals. In this manner, the indicator ring 500 provides the user with direct visual feedback about the strength of the force acting on the prosthetic hand or finger(s), and equivalently the strength exerted by the hand or finger(s) (e.g., the strength of a grip). In some embodiments, the LEDs include sections of different colors to further improve the intuitiveness of the visual signal. For example, the LEDs along the first two edges (starting from LED 503) may be green, the LEDs along the next two edges yellow or white, and the LEDs along the last two edges red. The mapping between force sensor outputs and the control signal input to the LED indicator ring 500 may be calibrated such that red LEDs alert the user that the exerted forces are too high.

Figure 6A:
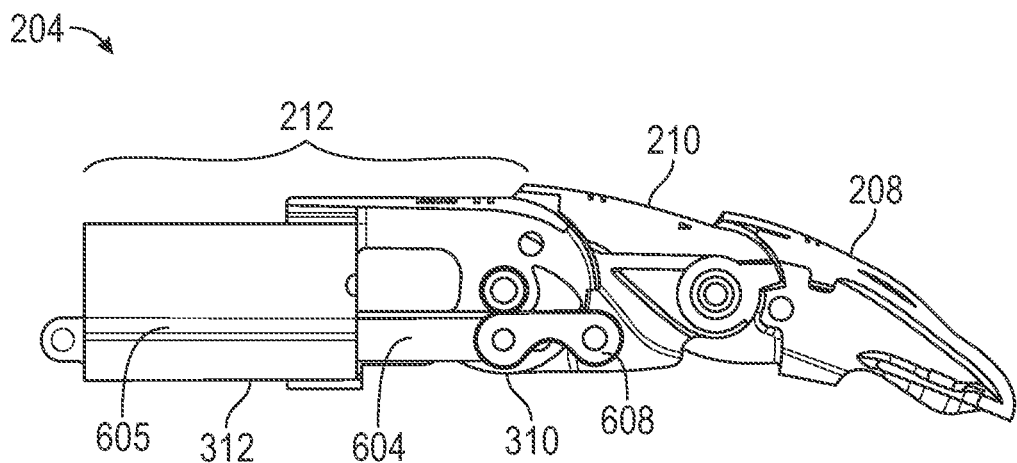
FIGS. 6A and 6B are side views of an example finger module of the prosthetic hand of FIGS. 2A-2C in extended and flexed configurations, respectively, illustrating finger movement and actuation.
Figure 6B:
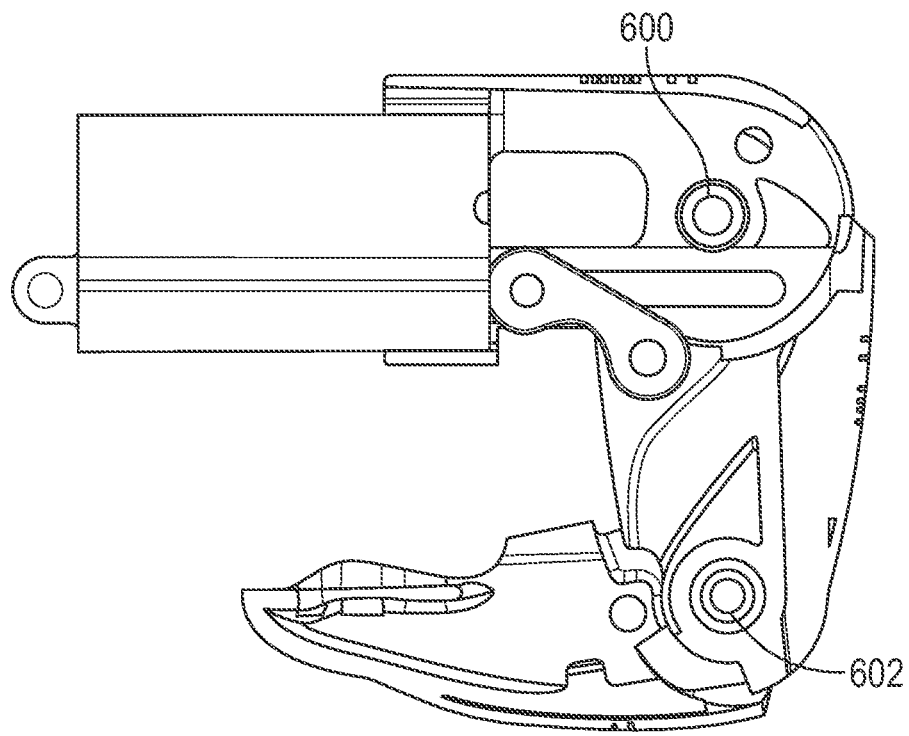

FIGS. 6A and 6B are side views of an example finger module 204 of the prosthetic hand 200 of FIGS. 2A-2C in extended and flexed configurations, respectively, illustrating the movement and actuation of the finger 204. As noted previously, the finger module 204 may be manufactured as a completely assembled unit including a distal phalanx 208, a proximal phalanx 210, and a knuckle section 212 including knuckle and motor housings 310, 312 that collectively contain the actuation mechanism and actuator motor (collectively the "actuator"). The finger module can be easily replaced by disassembling the palmar and dorsal plates 220, 222 of the palm module 206 of the prosthetic hand 200, removing the entire finger module 204, replacing it with another (provided) finger module 204, and then reassembling the palm module plates 220, 222 together.

The finger modules 204 may be disposed such that each pair of adjacent sections of the finger module 204 shares a common single degree-of-freedom rotary joint. For example, the knuckle section 212 and proximal phalanx 210 may share a joint 600 corresponding anatomically to the metacarpophalangeal (MCP) joint, while the proximal and distal phalanges 210, 208 share a joint 602 anatomically corresponding to a proximal interphalangeal (PIP) joint. The proximal and distal phalanges 208, 210 of each finger module 204 may be configured with tendon cables in a double-rocker four-bar linkage assembly/configuration, such that the angular motions of the linkages (that is, the phalanges 208, 210) in each finger module 204 are synchronized—resulting in two-dimensional (2D) planar motion. For instance, comparing FIGS. 6A and 6B, it can be seen that, as the proximal phalanx 210 rotates relative to the knuckle section 212 about the MCP joint 600 (e.g., as shown by ninety degrees), the distal phalanx 208 simultaneously rotates relative to the proximal phalanx 210 about the PIP joint 602 (e.g., also by ninety degrees), resulting in finger flexion.

The actuation of each finger module 204 may be achieved by one or more actuators, such as, in the depicted example, a linear (axially moving) actuator installed in the knuckle section 212 that includes an actuator rod 604 moved, via a lead screw 605, by an actuator motor inside the motor housing 312. The distal end of the actuator rod 604 may be connected via a drag link 608 to the proximal phalanx 210, such that actuation of the lead screw 605 and the resulting axial motion of the actuator rod 604 induce a torque about the MCP joint 600, thereby causing the proximal phalanx 210 of the finger module 204 to rotate about the MCP hinge pin, as depicted in FIG. 6B. Rotation of the proximal phalanx 210 relative to the knuckle section 212 may induce a subsequent rotation of the distal phalanx 208 with respect to the proximal phalanx 210. Since tendon cables are incapable of sustaining axial compressive forces, a torsion spring may be installed concentrically on the PIP pins in order to provide torque required to return the finger module 204 to an extended configuration (as shown in FIG. 6A).

In alternative finger module embodiments, the distal phalanx may be separated into a middle phalanx and a distal phalanx, for a total of three phalanges per finger, as noted previously. In this case, a second four-bar double rocker linkage may be formed such that rotation of the middle phalanx (caused by rotation of the proximal phalanx around the knuckle section) induces a subsidiary rotation of the distal phalanx around the middle phalanx. The linkage may be formed similarly by means of a cable connecting the distal end of the proximal phalanx to the palmar side of distal phalanx (travelling through a hollow section of the middle phalanx).

Figure 7A:
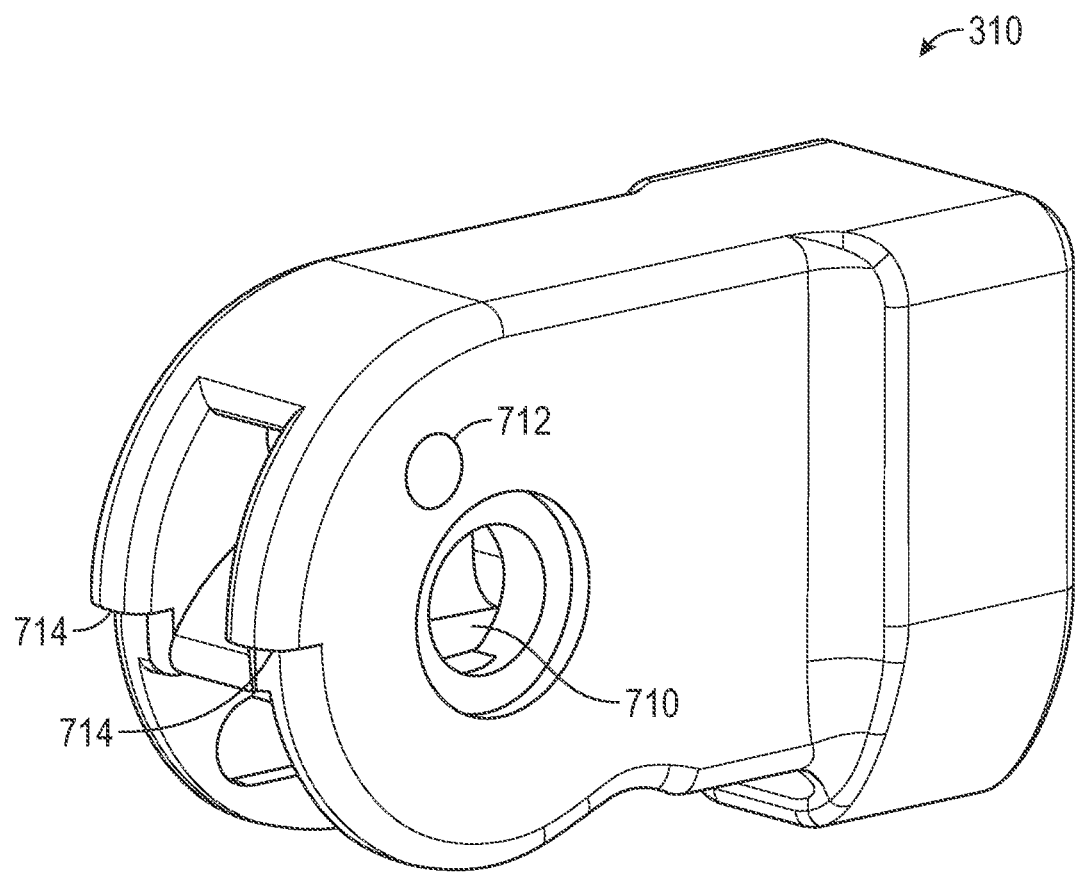
FIGS. 7A-7D are various views of portions of an example knuckle section as may be used in the finger module of FIGS. 6A and 6B, illustrating the actuation mechanism in more detail.
Figure 7B:
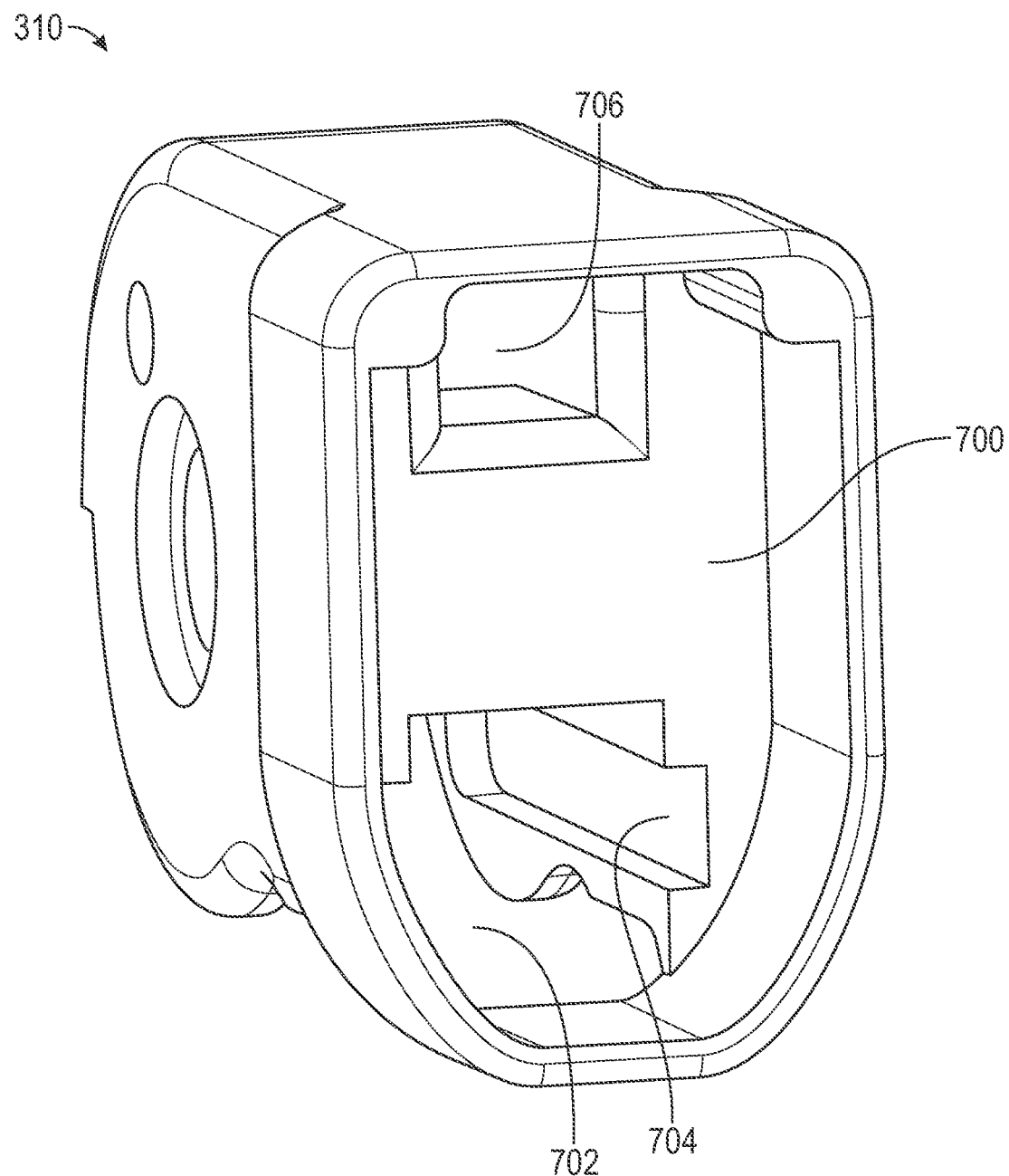
Figure 7C:
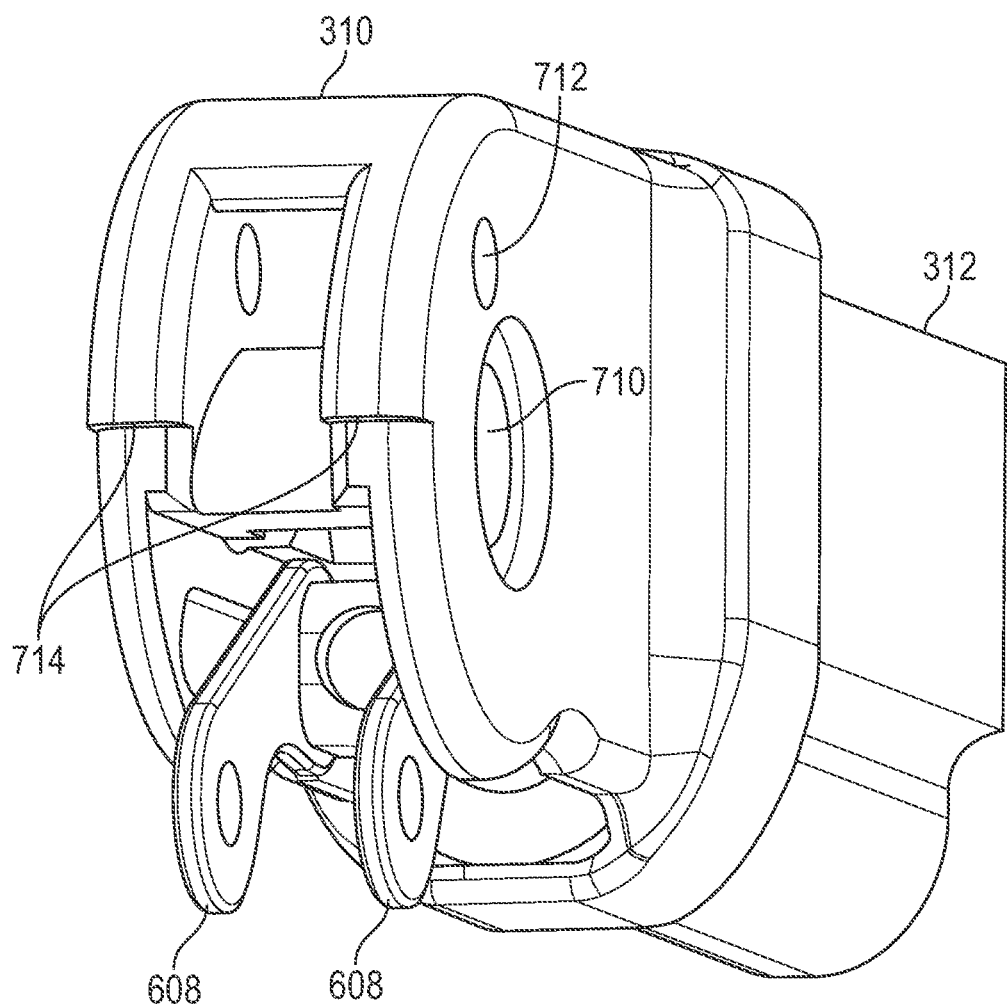
Figure 7D:
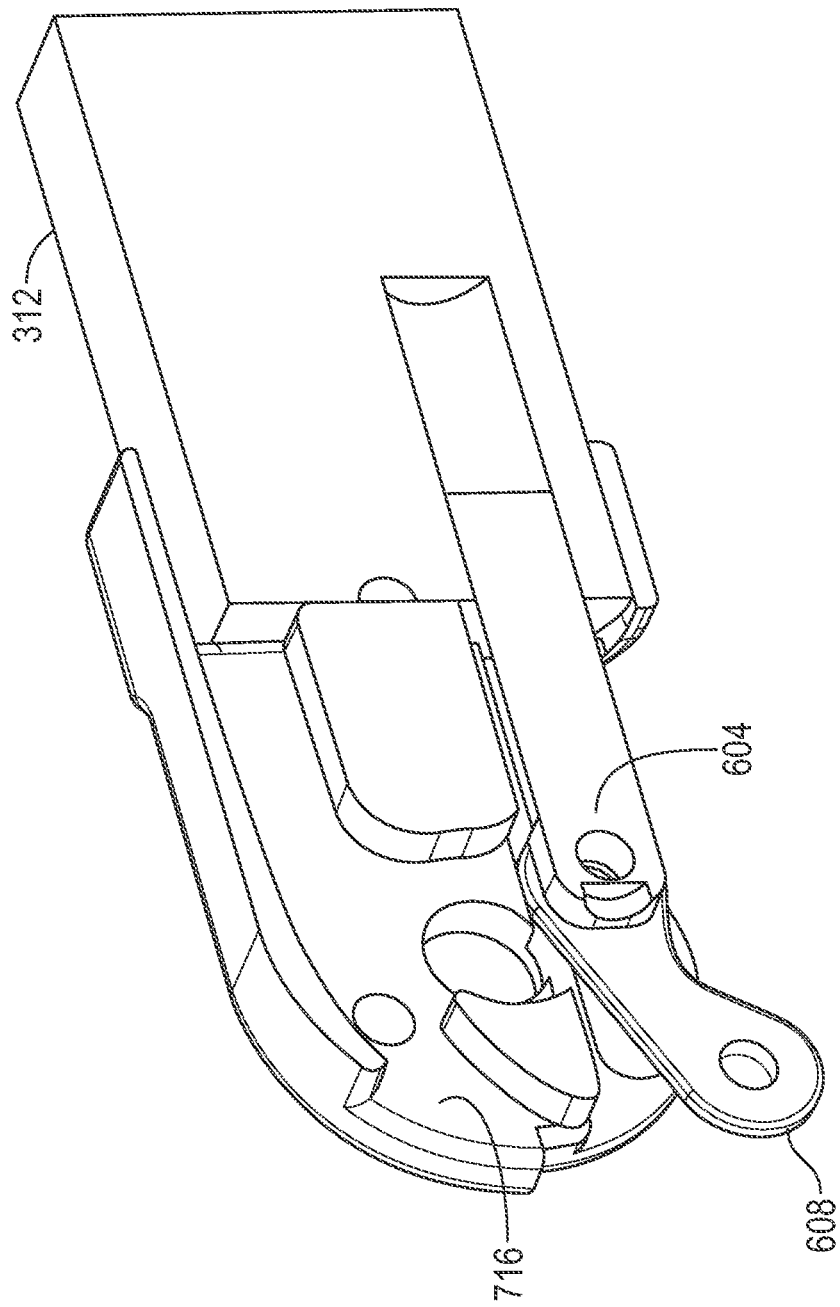

FIGS. 7A-7D are various views of portions of an example knuckle section 212 as may be used in the finger module 204 of FIGS. 6A and 6B, illustrating the actuation mechanism in more detail. FIGS. 7A and 7B show only the knuckle housing 310, at angles from the distal and proximal end, respectively, while FIGS. 7C and 7D show the knuckle housing 310 along with components of the actuation mechanism (actuator rod 604 and drag link 608) and motor housing 312 in full and cut-away perspective views. The knuckle section 212 may provide both a hinge point for the proximal phalanx 210 and a housing for the linear actuator. The linear actuator may be located within the palm module 202, for example, may be seated within a recess within the dorsal-facing side of the palmar plate 220. In another embodiment, as shown, the knuckle section 212 may retain or hold the linear actuator in the knuckle and motor housings 310, 312, and the knuckle section 212 itself may be partially or entirely housed within a cradle 300 in the palm module 202.

As shown in FIG. 7B, the knuckle housing 310 may include an open backside or receiver 700 that may be configured and dimensioned to receive a linear actuator motor (encased in housing 310). The knuckle housing 310 may also include an open frontal recess 702 that is configured and dimensioned to receive the linear actuator rod 604 to extend and retract therethrough. This recess 702 also may include rail guides 704, which contain the rod-end linkage pin. This pin connects the linear actuator rod 604 to the drag links 608, which are in turn connected to the proximal phalanx 210 of the finger module 204. Lastly, the knuckle housing 310 may also be configured and dimensioned to include one or more wiring channels 706 that may be located on the dorsal-facing side of the knuckle section 212. The one or more wiring channels 706 may be used for motor and/or force sensor electrical wiring to be routed back to the electronic control circuitry 112 (e.g., PCB) within the hand 102.

As shown in FIG. 7C, the proximal portion of the knuckle housing 310 includes a hinge area including a cylindrical bore 710 to seat a corresponding flanged bushing of the proximal end of the proximal phalanx 210 of the finger module 204. The hinge area may also comprise a cable tendon insertion pin through bore 712. The front (distal) end of the knuckle housing 310 may further include an external feature 714, referred to as a "pawl," that acts as a stop to prevent hyperextension of the proximal phalanx 210 during use of the prosthetic hand 200. Moreover, the hinge area may include an internal channel or recess 716 that runs underneath the exposed surface of the knuckle housing 310 and through the wiring channel and tendon cable channel in the knuckle housing 310.

Figure 8:
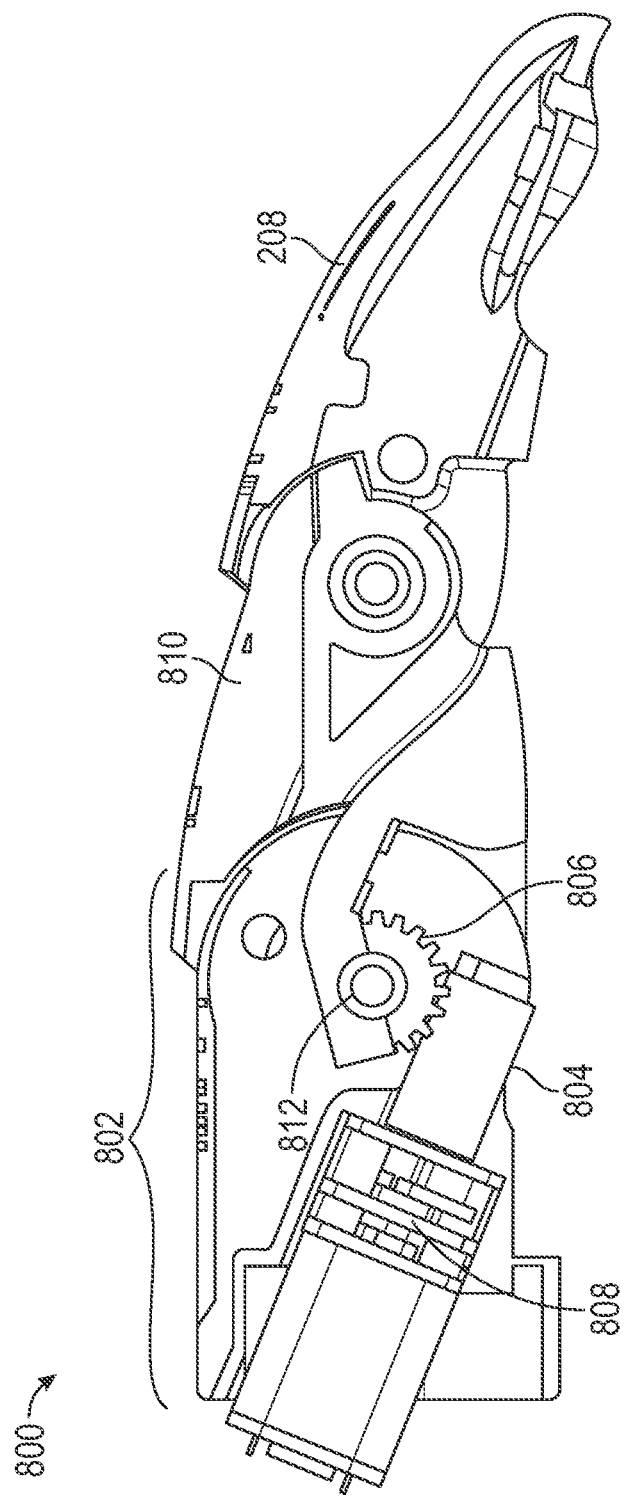
FIG. 8 is a side view of an alternative example finger module utilizing a different actuation mechanism, as may likewise be used in the prosthetic hand of FIGS. 2A-2C.

FIG. 8 is a side view of an alternative example finger module 800 utilizing a different actuation mechanism, as may likewise be used in the prosthetic hand 200 of FIGS. 2A-2C (as another implementation of finger module 204). In this alternative embodiment, the knuckle section 802 retains a worm gear assembly. The external geometry of the knuckle section 802 may be similar to that of the above-described knuckle housing 310 including the flanged bushings for thrust/radial loads. However, in this knuckle section 802, the internal geometry may differ, e.g., to define plain bearing surfaces to accommodate the worm helix 804 and worm gear 806 in a transverse-mounted arrangement.

A rotary servomotor 808 may actuate the worm gear assembly to induce rotation of the proximal phalanx 810 of the finger module 204. Rotation of the worm helix 804 induces a corresponding motion of the worm gear 806, which extends through an opening in the knuckle section 802 and is fastened to the proximal phalanx 810, concentric to the MCP joint 812. Excessive torque conditions may be prevented by employing the cantilevered worm gear mount in the proximal phalanx 810 as a calibrated drive clutch. Excessive torques can cause high reaction forces between worm gear 806 and helix 804, deflecting the cantilevered worm gear 806 away from the helical gear teeth, which could, in turn, de-couple the proximal phalanx 810 from the worm-gear drive. In an example embodiment, the force-governed engagement clutch will automatically re-engage when forces are reduced. Of course, the system will need to do an automatic "home position detection" since the worm gear assembly may have "skipped a tooth."

As will be readily appreciated, the described actuation mechanisms are merely examples, and various other mechanisms for actuating the prosthetic fingers may occur to those of ordinary skill in the art. For example, instead of using the worm gear assembly of FIG. 8, a pinion and bevel gear arrangement could be used (e.g., also in a transverse-mounted arrangement).

Figure 9A:
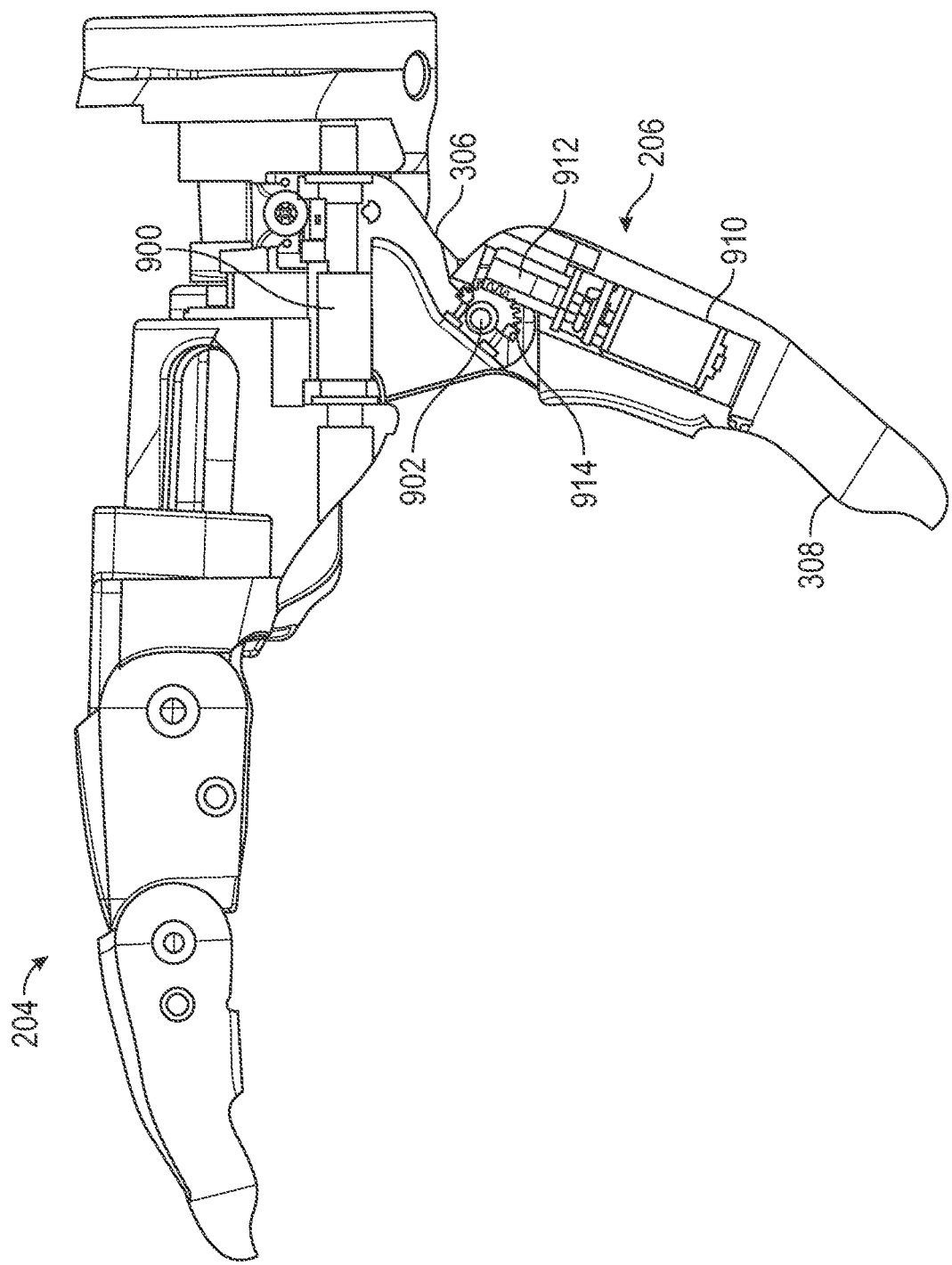
FIG. 9A is a side view of an example thumb module, shown alongside a finger module, of the prosthetic hand of FIGS. 2A-2C.
Figure 9B:
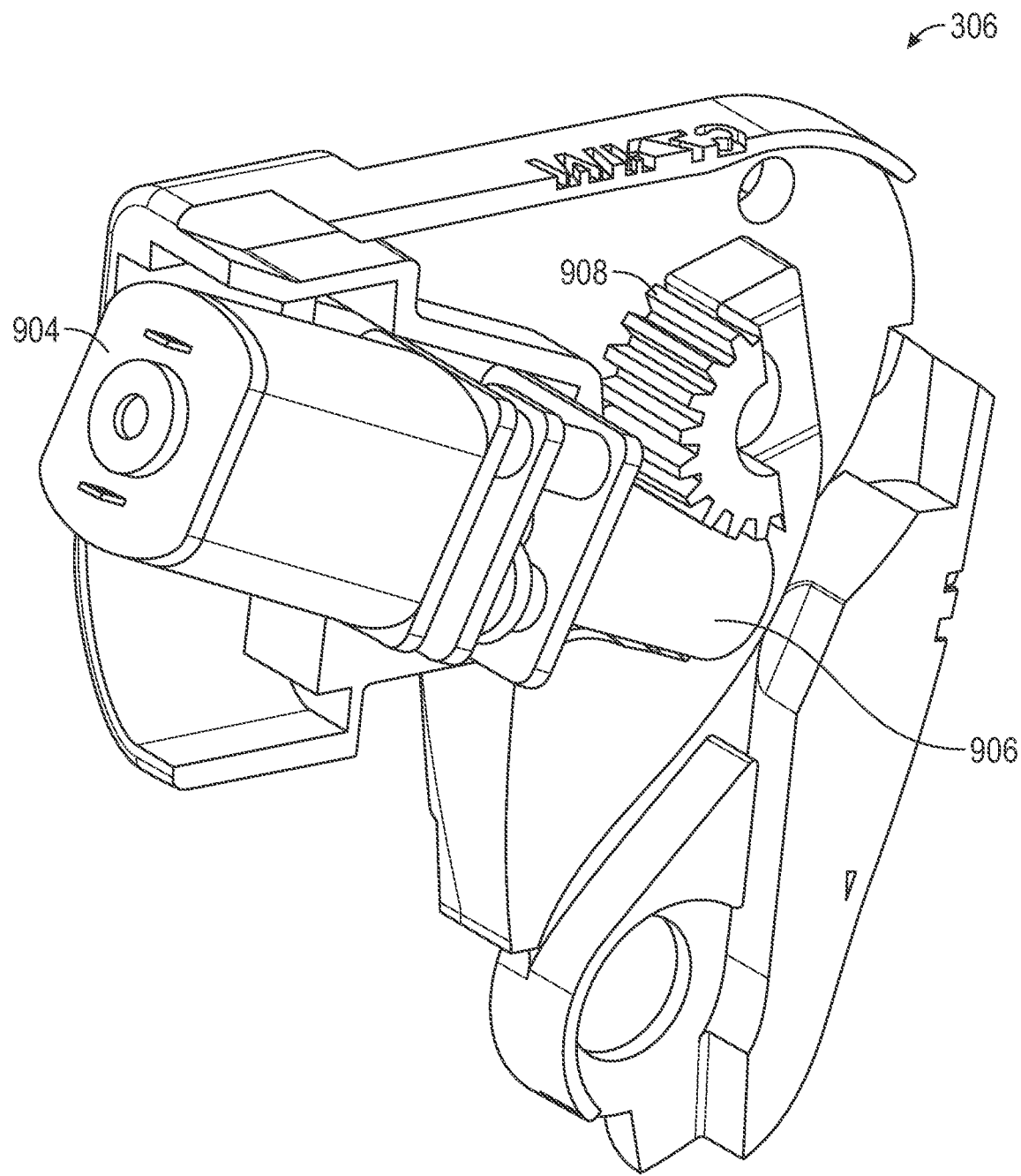
FIG. 9B illustrates the metacarpal of the thumb module and an associated actuation mechanism in more detail.

FIG. 9A is a side view of an example thumb module 206, shown alongside a finger module 204, of the prosthetic hand 200 of FIGS. 2A-2C. Like the finger modules 204, the thumb module 206 is attached to the palm module 202 of the prosthetic hand 100. In an example embodiment, the thumb module 206 includes a metacarpal section 306 and a phalanx 308. FIG. 9B illustrates the metacarpal 306 and an associated actuation mechanism in more detail. The thumb module 206 may include internal actuation mechanisms that differ from the finger modules 204 in that the thumb module 206 may include two joints arranged in a transverse configuration, allowing for a 3D spatial motion of the tip of the phalanx 308 of the thumb module 206 (achieving, in effect, rotational and/or flexural motion). For example, the metacarpal 306 may be configured with a rotary joint 900 to the palm module 202, herein also the carpometacarpal joint, and with a rotary hinge joint 902 to the phalanx 308. Rotation motion of the carpometacarpal joint 900 may be accomplished by a rotary gear motor 904 actuating a worm gear set, as shown in FIG. 9B. The worm gear set may include a worm gear 906 that, like the gear motor 904, is included in the palm module 202, and engages a gear 908 affixed to the metacarpal 306. Rotation of the worm gear 906 causes the metacarpal gear 908, and with it the metacarpal 306, to rotate about the carpometacarpal joint 900. Actuation about the joint 902 shared by the metacarpal 306 and the phalanx 308 of the thumb 206 may be achieved, as shown in FIG. 9A, by a rotary gear motor 910 and worm gear 912 included in the phalanx 208, and a gear 914 affixed to the metacarpal 306 that engages the worm gear 912.

In the embodiment of FIGS. 9A and 9B, both rotation and flexion/extension are accomplished by worm gear assemblies. In an alternative embodiment, the thumb module 206 may achieve flexural and/or extension motion of the using a linear actuator (similar to the one described above with respect to the finger module 204). In this embodiment, a lead screw actuator, for example, may achieve flexion of the thumb module 206, while a torsional spring may be incorporated into the thumb module 206 to achieve extension of the thumb module 206.

Having described structure and function of a prosthetic hand in accordance with various embodiments, we now turn to methods of manufacturing such devices. Conventional prosthetic limbs are typically made from high-strength materials using expensive professional machining or injection molding techniques. By contrast, in accordance with various embodiments, additive manufacturing techniques (commonly referred to as "3D printing"), such as, e.g., multi jet fusion (MJF), stereolithography (SLA), or metal sintering, are used to make some or all structural components of the disclosed devices (e.g., finger and thumb phalanges, knuckle housings, metacarpals, and/or the palmar and dorsal plates). 3D printing can achieve medium- to high-volume production of prosthetic device parts at comparatively low cost. Further, innovations in material science have provided strong and robust 3D-printable plastics and composites, including, for example, carbon-fiber-reinforced composites and high-performance plastics like Polyamide 11 (PA11, also called "Nylon 11") and Polyamide 12 (PA12, also "Nylon 12"). PA11 is a bioplastic polyamide powder derived from vegetable/castor oil, and PA12 is a synthetic powder cultivated from petroleum materials. Both materials are known for the toughness, tensile strength, and the ability to flex without fracture, and can optionally be reinforced, e.g., with fiberglass, fiberglass beads, titanium or aluminum alloys, or other reinforcement-type materials. In various embodiments, prosthetic device components are 3D-printed from such high-performance materials, resulting in reduced manufacturing cost without loss of structural or material integrity. However, as will be appreciated, the manufacture of structural prosthetic device components as disclosed herein is limited neither to plastics and composites nor to 3D printing. For example, some components may alternatively be manufactured from metal or metal alloys, whether by 3D printing or otherwise. Further, certain components, such as the palmar and dorsal plates, may be amenable to manufacture using convention techniques, like injection molding.

Unlike traditional techniques such as injection molding, which are unable to produce complex organic shapes, additive manufacturing such as MJF allows creating parts with complex internal geometries. This capability is leveraged, in various embodiments, to implement modular prosthetic device designs as disclosed herein. The modular design, and the easy of assembly and repair it entails, can contribute substantially to reducing the cost of prosthetic devices. Additive manufacturing and modular design, especially when used in conjunction, can provide prosthetic devices that are much more affordable than conventional prosthetic devices available in the industry.

Additive manufacturing also allows for functionally integrated parts, that is, parts that monolithically integrate structural components with mechanically functional parts like gears, clutches, bearings, drive-train components, etc. To further illustrate, functional integration may achieve monolithic components including various combinations of power transmission elements (e.g., couplings, pawls, keyslots, splines), locating surfaces (e.g., bushings, flanges, precision bores), fastening elements (e.g., clips, tabs, bosses), and structural elements (e.g., struts, beams, tubes). Functional integration can provide cost savings, as well as increase mechanical robustness of the monolithic part by eliminating, e.g., mating surfaces and small fasteners that would otherwise act as points of high stress that make the area prone to failure. FIGS. 10A-11B provides examples of functional integration.

Figure 10A:
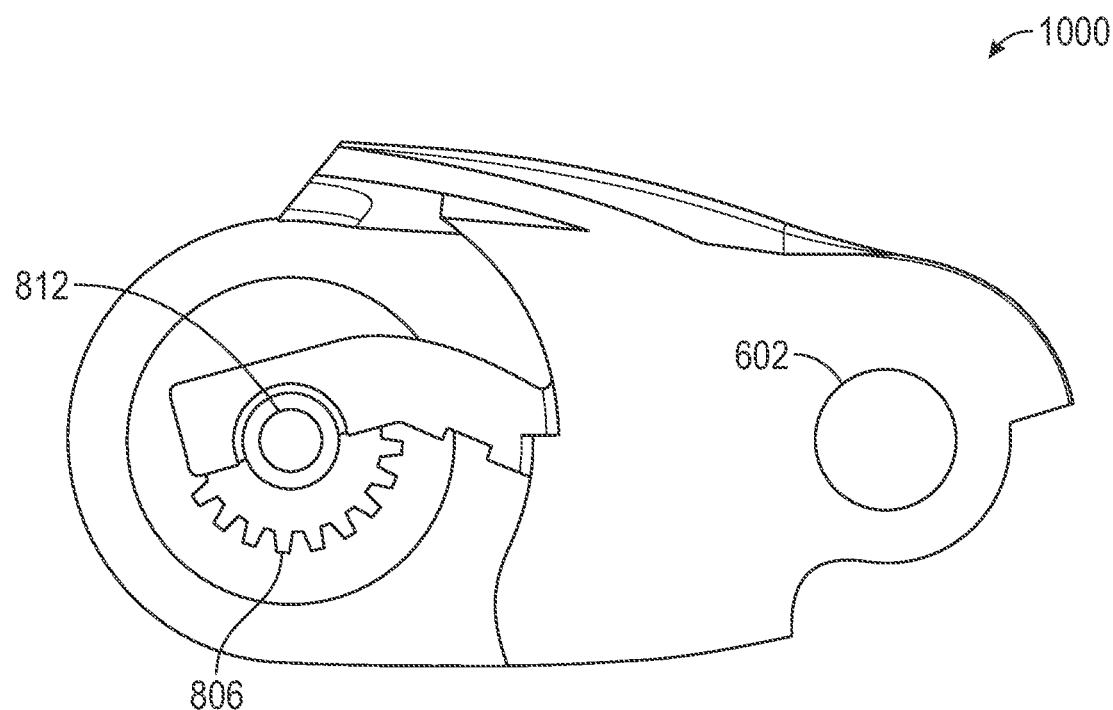
FIGS. 10A and 10B are side views of conventional and functionally integrated embodiments, respectively, of the proximal phalanx of an example finger module as shown in FIG. 8.
Figure 10B:
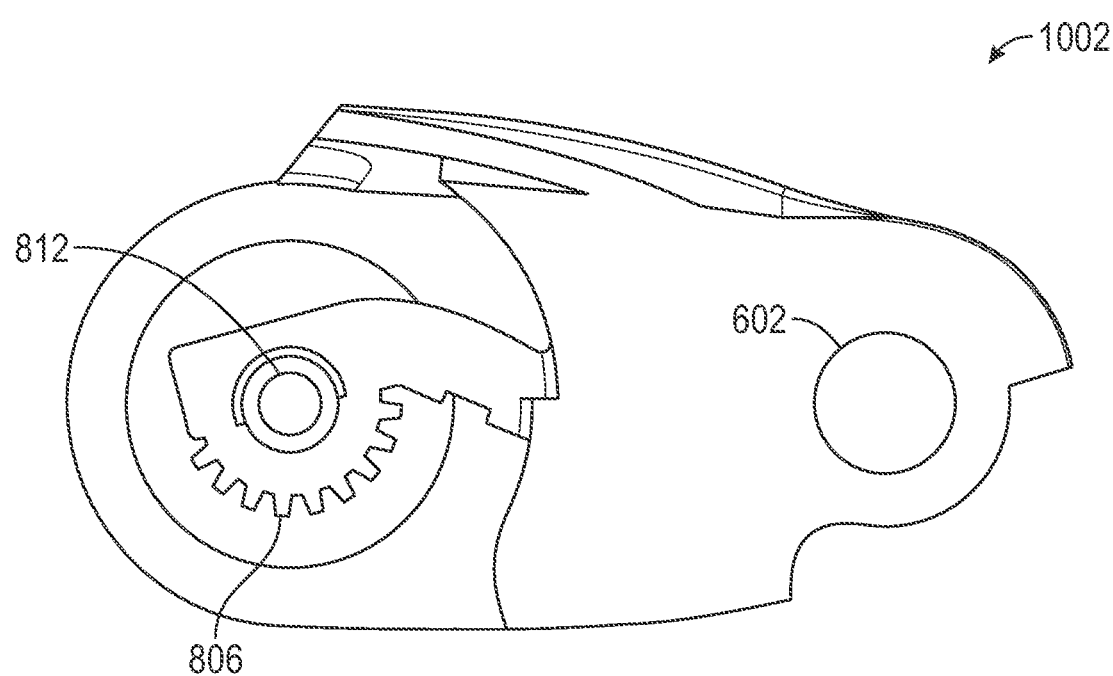

FIGS. 10A and 10B are side views of conventional and functionally integrated embodiments, respectively, of the proximal phalanx 810 of an example finger module 800 as shown in FIG. 8. Within the finger module 800, the proximal phalanx 810 is connected to a knuckle section 802 at an MCP joint 812, and to the distal phalanx 208 at a PIP joint 602. At MCP joint 812, the proximal phalanx 810 includes a gear 806. That gear 806 may be separately machined and then connected to the structural part of the proximal phalanx 810 to create the overall sub-assembly 1000, as depicted in FIG. 10A. Alternatively, using functional integration via 3D printing, the gear 806 may be directly printed onto the structural part, resulting in a single, monolithic component 1002, as shown in FIG. 10B.

Figure 11A:
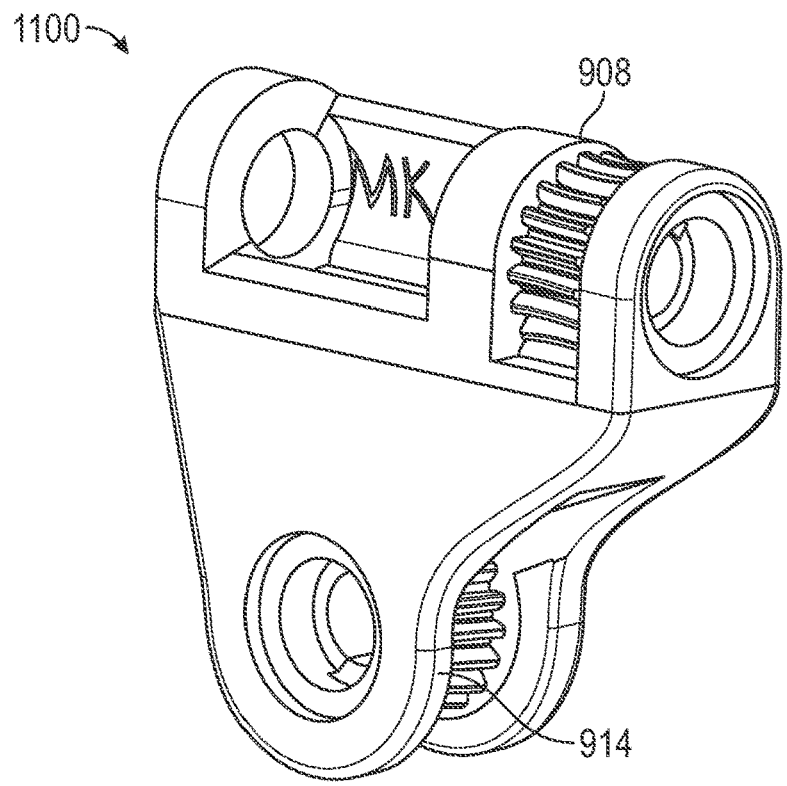
FIGS. 11A and 11B are perspective views of conventional and functionally integrated embodiments, respectively, of a metacarpal of an example thumb module as shown in FIGS. 9A and 9B.
Figure 11B:
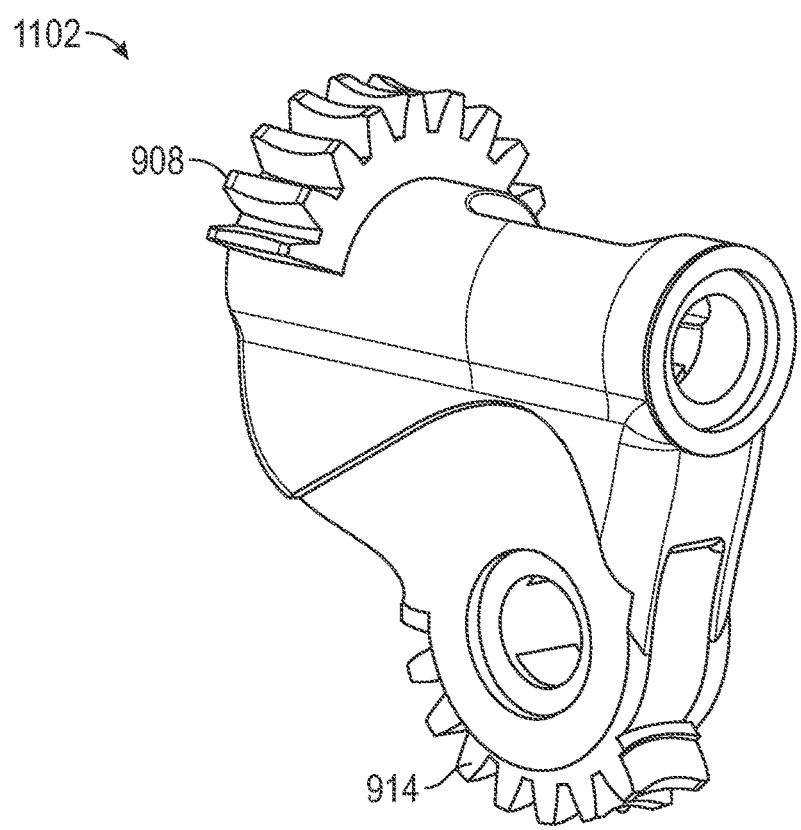

FIGS. 11A and 11B are perspective views of conventional and functionally integrated embodiments, respectively, of a metacarpal 306 of an example thumb module 206 as shown in FIGS. 9A and 9B. The metacarpal 306 includes two gears 908, 914, one (gear 908) at the carpometacarpal joint 900 for engagement with a worm gear 906 of an actuator placed in the palm module 202 (see FIG. 9A), and the other (gear 914) at a joint 902 shared with the phalanx 308 of the thumb module 206 for engagement with a worm gear 912 of an actuator placed in the phalanx 308. The gears 908, 914 may be separately machined and then connected to the structural part of the metacarpal 306 to create the overall sub-assembly 1100, as depicted in FIG. 11A. Alternatively, using functional integration via 3D printing, the gears 908, 914 may be directly printed onto the structural part, resulting in a single, monolithic component 1102, as shown in FIG. 11B.

Aside from functionally integrated parts, other design features may contribute to better robustness, in accordance with various embodiments. For example, conventional prosthetic fingers often utilize actuation cables that run through multiple phalanx sections, resulting in rapid wear when the cable is dragged around a corner during flexion. In some embodiments as described herein, the actuation cable is replaced by a rigid link, eliminating this issue. Alternatively, in some embodiments, an actuation cable may be used, but installed between the finger actuator and proximal phalanx in a manner unlikely to skive, abrade, or suffer from off-axis or compression forces. As another example, conventional prosthetic designs sometimes use complicated detent clutches, which are robust in the rotary direction, but subject to failure when loaded from the side. A detent clutch may, for example, protect a finger sub-assembly from experiencing over-torque in the rotary direction, but cannot protect from excessive forces in orthogonal direction; thus, a force in a transverse direction to the clutch actuation direction may still lead to failure. Some embodiments described herein utilize, instead, lead-screw actuators that may overhaul and unwind if an applied force exceeds a rated amount, avoiding catastrophic breaking.

In various embodiments, the structural and functional parts of the prosthetic limb, such as the palmar module 202 and phalanges of the finger and thumb modules 204, 206, are covered by a layer of compliant material, such as silicone or some type of rubber/synthetic material (e.g., urethane rubber, rubber, or similar material), that mimics the skin. In examples, the exterior material layer provides a compliant surface with a high coefficient of friction (e.g., to allow the prosthetic hand user to easily grip and hold objects). The thickness of this exterior material layer may range from 1.00 mm to 8.00 mm. The exterior layer may be bonded to the surfaces of the structural parts by a suitable adhesive, or applied by overmolding. In an overmold process, the structural part (e.g., a phalanx or palm module) that will make up the core of the component is placed inside a mold, defining a cavity, or negative space, between the structural part and the interior surface of the mold. A mixture of the selected material for the skin (e.g., urethane or silicone) is then poured into the negative space of the mold, e.g., via a tunnel, to fill the negative space and cure into the desired shape.

In embodiments that use force sensors (e.g., force-sensitive resistor or micro-force transducers), these sensors may be disposed beneath the exterior layer serving as a synthetic skin (e.g., at a depth between 1.00 mm and 8.00 mm), which can improve force sensing capabilities. Force sensors may be integrated or formed within the palm or fingertips of a prosthetic hand via the process of overmolding. The force sensors may be attached to the surface of a prosthetic part, such as the palmar surface of the palm module or the fingertips, using an adhesive. During overmolding, as described above, the prosthetic part, along with the attached force sensor(s), is placed inside of a mold, and with the force sensor remaining in position, a suitable material is added into the mold and cured in place. A particularly suitable material is urethane, which aids in forming a compliant fingertip grip while effectively transmitting physical forces to the underlying force sensors.

While principles of the disclosed subject matter are described herein with reference to illustrative embodiments for particular applications, it should be understood that the disclosure is not limited thereto. Those having ordinary skill in the art and access to the teachings provided herein will recognize additional modifications, applications, embodiments, and substitutions within the scope of the disclosed subject matter.

What is claimed is:

1. A modular prosthetic hand comprising:
a palm module comprising a palmar plate and a dorsal plate separably affixed to each other and collectively defining a plurality of knuckle cradles; and
a plurality of finger modules each comprising a knuckle section releasably attached to the palm module within a corresponding one of the knuckle cradles,
wherein a surface portion of each knuckle cradle geometrically conforms to a mating surface portion of the corresponding knuckle section,
wherein, when the palmar and dorsal plates are separated, each knuckle section is insertable into and removable from a palmar portion of the corresponding knuckle cradle in a direction normal to a plane of the palmar plate or insertable into and removable from a dorsal portion of the corresponding knuckle cradle in a direction normal to a plane of the dorsal plate, and
wherein, when the palmar and dorsal plates are fastened to each other, movement of the knuckle section relative to the palm module is fully constrained by an interlocking fit between the knuckle cradle and the corresponding knuckle section in which the surface portion of the knuckle cradle blocks movement of the knuckle section.

2. The modular prosthetic hand of claim 1, wherein each finger module further comprises a proximal phalanx and a distal phalanx, the proximal phalanx being attached to the knuckle section by a first rotary hinge joint, the knuckle section comprising an actuation mechanism and associated actuator motor configured to cause rotation of the proximal phalanx about the first rotary hinge joint.

3. The modular prosthetic hand of claim 2, wherein the distal phalanx is attached to the proximal phalanx via a second rotary hinge joint, the proximal and distal phalanges being configured in a double-rocker four-bar linkage, such that rotation of the proximal phalanx about the first rotary hinge joint causes a coordinated rotation of the distal phalanx about the second rotary hinge joint.

4. The modular prosthetic hand of claim 2, wherein the palm module comprises electronic control circuitry to control the actuator motors of the plurality of finger modules.

5. The modular prosthetic hand of claim 4, wherein each of the finger modules further comprises a position transducer associated with the respective actuation mechanism and electrical wiring for connecting the actuator motor and the position transducer to the electronic control circuitry.

6. The modular prosthetic hand of claim 5, wherein the actuator motor and the position transducer are parts of a servomotor.

7. The modular prosthetic hand of claim 4, wherein one or more of the finger modules each comprise a force sensor to measure an external force acting on the finger module and electrical wiring for connecting the force sensor and the actuator motor to the electronic circuitry.

8. The modular prosthetic hand of claim 7, wherein the force sensor is placed at a tip of the distal phalanx of the respective finger module.

9. The modular prosthetic hand of claim 7, wherein the palm module further comprises a visual indicator configured to indicate a strength of the external force.

10. The modular prosthetic hand of claim 9, wherein the visual indicator comprises a light-emitting diode (LED) indicator ring.

11. The modular prosthetic hand of claim 1, further comprising a wrist module having an electric quick disconnect (EQD) coupling mechanism for connection to a prosthetic socket.

12. The modular prosthetic hand of claim 11, wherein the palm module comprises a mounting recess to which the wrist module is releasably attached.

13. The modular prosthetic hand of claim 1, further comprising a thumb module comprising a metacarpal section releasably attached to the palm module.

14. A modular prosthetic hand comprising:
a palm module;
a plurality of motorized finger modules movably attached to the palm module;
electronic control circuitry contained in the palm module to, responsively to one or more myoelectric signals, configure the plurality of motorized finger modules to exert a grip;
force sensors integrated into the prosthetic hand, including into distal phalanges of the finger modules, to measure external forces acting on the prosthetic hand, including on the distal phalanges of the finger modules, when the prosthetic hand is in contact with an external object during the grip;
electrical wires to route electrical outputs of the force sensors in the distal phalanges of the finger modules back through the finger modules to the electronic control circuitry; and
a visual indicator within the palm module, communicatively coupled to the electronic control circuitry and configured to indicate a strength of the grip based on a control signal generated by the electronic control circuitry from the electrical outputs of the force sensors,
wherein the finger modules are releasably attached to the palm module and the electrical wires are reversibly connected to the electronic control circuitry.

15. The modular prosthetic hand of claim 14, wherein the visual indicator comprises a ring of LEDs configured to sequentially light up as the strength of the one or more external forces increases from a set first strength to a set second strength.

16. The modular prosthetic hand of claim 15, wherein the ring of LEDs comprises multiple sections having LEDs of multiple respective colors.

17. The modular prosthetic hand of claim 14, wherein the force sensors comprise force sensors placed at tips of the finger modules.

18. The modular prosthetic hand of claim 14, comprising an exterior layer of compliant material, wherein the force sensors are placed underneath the exterior layer.

19. The modular prosthetic hand of claim 14, wherein the force sensors comprise force-sensing resistors.

* * * * *